US011434494B2

(12) United States Patent
Beetham et al.

(10) Patent No.: US 11,434,494 B2
(45) Date of Patent: Sep. 6, 2022

(54) TARGETED GENE MODIFICATION USING OLIGONUCLEOTIDE-MEDIATED GENE REPAIR

(71) Applicants: CIBUS US LLC, San Diego, CA (US); CIBUS EUROPE B.V., AD Kapelle (NL)

(72) Inventors: Peter R. Beetham, Carlsbad, CA (US); Gregory F. W. Gocal, San Diego, CA (US); Christian Schopke, Carlsbad, CA (US); Noel Joy Sauer, Oceanside, CA (US); James Pearce, La Jolla, CA (US); Rosa E. Segami, Escondido, CA (US); Jerry Mozoruk, Encinitas, CA (US)

(73) Assignees: CIBUS US LLC, San Diego, CA (US); CIBUS EUROPE B.V., Breda (NL)

( * ) Notice: Subject to any disclaimer, the term of this patent is extended or adjusted under 35 U.S.C. 154(b) by 0 days.

(21) Appl. No.: 14/777,410

(22) PCT Filed: Mar. 14, 2014

(86) PCT No.: PCT/US2014/029621
§ 371 (c)(1),
(2) Date: Sep. 15, 2015

(87) PCT Pub. No.: WO2014/144987
PCT Pub. Date: Sep. 18, 2014

(65) Prior Publication Data
US 2016/0304892 A1  Oct. 20, 2016

Related U.S. Application Data

(60) Provisional application No. 61/801,320, filed on Mar. 15, 2013.

(51) Int. Cl.
*C12N 15/82* (2006.01)
(52) U.S. Cl.
CPC ................................ *C12N 15/8213* (2013.01)
(58) Field of Classification Search
None
See application file for complete search history.

(56) References Cited

U.S. PATENT DOCUMENTS

| | | | |
|---|---|---|---|
| 4,945,050 A | 7/1990 | Sanford et al. | |
| 5,008,200 A | 4/1991 | Ranch et al. | |
| 5,024,944 A | 6/1991 | Collins et al. | |
| 5,100,792 A | 3/1992 | Sanford et al. | |
| 5,204,253 A | 4/1993 | Sanford et al. | |
| 5,302,523 A | 4/1994 | Coffee et al. | |
| 5,334,711 A | 8/1994 | Sproat et al. | |
| 5,484,956 A | 1/1996 | Lundquist et al. | |
| 5,489,520 A | 2/1996 | Adams et al. | |
| 5,750,673 A | 5/1998 | Martin | |
| 5,756,325 A | 5/1998 | Kmiec | |
| 5,760,012 A | 6/1998 | Kmiec et al. | |
| 5,780,296 A | 7/1998 | Holloman et al. | |
| 5,795,972 A | 8/1998 | Kmiec | |
| 5,871,984 A | 2/1999 | Kmiec | |
| 5,888,983 A | 3/1999 | Kmiec et al. | |
| 5,945,339 A | 8/1999 | Holloman et al. | |
| 6,004,804 A | 12/1999 | Kumar et al. | |
| 6,010,907 A | 1/2000 | Kmiec et al. | |
| 6,870,075 B1 | 3/2005 | Beetham et al. | |
| 9,512,444 B2 * | 12/2016 | Chen | ...................... C12N 15/85 |
| 2003/0084473 A1 | 5/2003 | Gocal et al. | |
| 2009/0205064 A1 * | 8/2009 | Schopke | .................. C12N 9/88 800/260 |
| 2012/0282699 A1 * | 11/2012 | Bundock | ............ C12N 15/8213 435/468 |
| 2013/0137180 A1 | 5/2013 | Chen et al. | |
| 2014/0068797 A1 * | 3/2014 | Doudna | ............... C12N 15/102 800/18 |

FOREIGN PATENT DOCUMENTS

| | | |
|---|---|---|
| EA | 201401319 A | 5/2015 |
| EP | 0629387 A1 | 12/1994 |
| EP | 0679657 A2 | 11/1995 |
| JP | 2010539986 A | 12/2010 |
| WO | 9849350 A1 | 11/1998 |
| WO | 9907865 A1 | 2/1999 |
| WO | 9940789 A1 | 8/1999 |
| WO | 9958702 A1 | 11/1999 |

(Continued)

OTHER PUBLICATIONS

Smetana et al. Non-apoptotic programmed cell death with paraptotic-like features in bleomycin-treated plant cells is suppressed by inhibition of ATM/ATR pathways or NtE2F overexpression. J. Exp. Bot. Apr. 2012;63(7):2631-44. Epub Jan. 20, 2012.*

Zhu et al. Engineering herbicide-resistant maize using chimeric RNA/DNA oligonucleotides. Nat Biotechnol. May 2000;18(5):555-8.*

Suzuki et al. Low-dose bleomycin induces targeted gene repair frequency in cultured melan-c cells using chimeric RNA/DNA oligonucleotide transfection. Int. J. Mol. Med. Jul. 2003;12(1):109-14.*

Vorobjev et al. Site-specific cleavage of RNA and DNA by complementary DNA—bleomycin A5 conjugates. Bioconj. Chem Nov.-Dec. 2003; 14(6):1307-13.*

Chen et al. I High-frequency genome editing using ssDNA oligonucleotides with zinc-finger nucleases. Nat Methods. Jul. 17, 2011;8(9):753-5.*

(Continued)

*Primary Examiner* — Cynthia E Collins
(74) *Attorney, Agent, or Firm* — Acuity Law Group, PC; Michael A. Whittaker

(57) ABSTRACT

The invention provides to improved methods for the modification of genes in plant cells, and plants and seeds derived therefrom. More specifically, the invention relates to the increased efficiency of targeted gene mutation by combining gene repair oligonucleotides with approaches that enhance the availability of components of the target cell gene repair mechanisms.

7 Claims, 13 Drawing Sheets

Specification includes a Sequence Listing.

(56) References Cited

FOREIGN PATENT DOCUMENTS

| WO | 9958723 | A1 | 11/1999 |
|---|---|---|---|
| WO | 0115740 | A1 | 3/2001 |
| WO | 2009046334 | A1 | 4/2009 |
| WO | 2011078662 | A1 | 6/2011 |
| WO | 2012012738 | A1 | 1/2012 |
| WO | 2012149470 | A1 | 11/2012 |
| WO | 2013009825 | A1 | 1/2013 |
| WO | 2013176772 | A1 | 11/2013 |
| WO | 2014144987 | A2 | 9/2014 |

OTHER PUBLICATIONS

Zhang et al. High frequency targeted mutagenesis in *Arabidopsis thaliana* using zinc finger nucleases. Proc Natl Acad Sci U S A. Jun. 29, 2010;107(26):12028-33. Epub May 27, 2010.*
Papaioannou et al. Oligonucleotide-directed gene-editing technology: mechanisms and future prospects. Expert Opin Biol Ther. Mar. 2012;12(3):329-42. Epub Feb. 10, 2012. Review. (Year: 2012).*
Bedell et al. In vivo genome editing using a high-efficiency TALEN system. Nov. 1, 2012;491(7422):114-8. Epub Sep. 23, 2012. (Year: 2012).*
Zhang et al. Transcription activator-like effector nucleases enable efficient plant genome engineering. Plant Physiol. Jan. 2013;161(1):20-7. Epub Nov. 2, 2012. (Year: 2013).*
Wang, Z. et al. Oligonucleotides 18, 21-32 (2008). (Year: 2008).*
Olsen, P.A. et al. DNA Repair (Amst.) 8, 298-308 (2009). (Year: 2009).*
Aarts, M. & te Riele, H. Nucleic Acids Res. 38, 6956-6967 (2010). (Year: 2010).*
Ferrara, L., Parekh-Olmedo, H. & Kmiec, E. B. DNA damage increases the frequency of gene repair in mammalian cells. Experimental Cell Res. 300, 170-179 (2004). (Year: 2004).*
Ferrara, L. & Kmiec, E. B. Camptothecin enhances the frequency of oligonucleotide-directed gene repair in mammalian cells by inducing DNA damage and activating homologous recombination. Nucleic Acids Res. 32, 5239-5248 (2004). (Year: 2004).*
Radecke, F. et al. Targeted chromosomal gene modification in human cells by single-stranded oligodeoxynucleotides in the presence of a DNA double-strand break. Mol Ther. 14, 798-808 (2006). (Year: 2006).*
Bonner, M. & Kmiec, E.B. DNA breakage associated with targeted gene alteration directed by DNA oligonucleotides. Mutat. Res. 669(1-2), 85-94. (2009). (Year: 2009).*
Rios et al. Stable Gene Targeting in Human Cells Using Single-Strand Oligonucleotides with Modified Bases. PLoS ONE 7, e36697, 2012. (Year: 2012).*
Liu et al. (2009) Cell Death Caused by Single-Stranded Oligodeoxynucleotide-Mediated Targeted Genomic Sequence Modification. Oligonucleotides 19: 281-286. (Year: 2009).*
Olsen et al. Genomic sequence correction by single-stranded DNA oligonucleotides: role of DNA synthesis and chemical modifications of the oligonucleotide ends. J. Gene Med. Dec. 2005;7(12):1534-44. (Year: 2005).*
Chen et al., High-frequency genome editing using ssDNA oligonucleotides with zinc-finger nucleases. Nat Methods. Jul. 17, 2011;8(9):753-755.
Office Action issued by SIPO in PRC Patent Application No. 2014800247089 dated Nov. 2, 2016—incl Engl lang transl Search Report only.
The Extended European Search Report issued EP 14763072 dated Aug. 23, 2016.
Ferrara and Kmiec, Camptothecin enhances the frequency of oligonucleotide-directed gene repair in mammalian cells by inducing DNA damage and activating homologous recombination. Nucleic Acids Res. Oct. 5, 2004;32(17):5239-5248.
Ferrara et al., Enhanced oligonucleotide-directed gene targeting mammalian cells following treatment with DNA damaging agents. Exp Cell Res. Oct. 15, 2004;300(1):170-179.
Wang et al., Single-stranded oligonucleotide-mediated gene repair in mammalian cells has a mechanism distinct from homologous recombination repair. Biochem Biophys Res Commun. Nov. 24, 2006;350(3):568-573.
The International Search Report and Written Opinion issued Oct. 10, 2014 in PCT/US2014/02962 (12 pages).
Puchta et al., "Role of Human Disease Genes for the Maintenance of Genome Stability in Plants" IN: Induced Plant Mutations in the Genomics Era, edited by Q.Y. Shu Rome: Food and Agriculture Organization of the United Nations, 2009, pp. 129-132.
Zarytova et al., "Synthesis of bleomycin AS oligonucleotide derivatives and site-specific cleavage of the DNA target", Bioconjug Chem, 1993, 4(3):189-193.
Office Action issued by the JPO in Japanese Patent Application No. 2016-503169 dated Dec. 12, 2017, 13 pages—incl Eng lang transl.
Sommer et al., Reporter system for the detection of in vivo gene conversion: changing colors from blue to green using GFP variants. Mol Biotechnol. Jun. 2006;33(2):115-122.
Office Action issued by EPO in European Patent Application No. 14763072.7 dated Jul. 18, 2017, 5 pages.
Tovkach et al., A toolbox and procedural notes for characterizing novel zinc finger nucleases for genome editing in plant cells. Plant J. Feb. 2009,57(4):747-757.
The International Preliminary Report on Patentability issued in PCT/US2014/029621 dated Sep. 15, 2015, 7 pages.
Altschul et al., Basic local alignment search tool. J Mol Biol. Oct. 5, 1990;215(3):403-410.
Altschul, et al., Gapped BLAST and PSI-BLAST; A New Generation of Protein Database Search Programs. Nucleic Acids Res. Sep. 1, 1997;25(17):3389-3402.
Arimondo et al., Recognition and cleavage of DNA by rebeccamycin- or benzopyridoquinoxaline conjugated of triple helix-forming oligonucleotides. Bioorg Med Chem. Apr. 2000;8(4):777-784.
Barsby et al., A Rapid and Efficient Alternative Procedure for the Regeneration of Plants from Hypocotyl Protoplasts of *Brassica napus*. Plant Cell Rep. Apr. 1986;5(2):101-103.
Bendinskas et al., Sequence-Specific Photomodification of DNA by an Oligonucleotide-Phenanthrodihydrodioxin Conjugate. Bioconjug Chem. Sep.-Oct. 1998;9(5):555-563.
Cermak et al., Efficient design and assembly of custom TALEN and other TAL effector-based constructs for DNA targeting. Nucleic Acids Res. Jul. 2011;39(12):e82.
Chuong et al., A Simple Culture Method for *Brassica hypototyl* Protoplasts. Plant Cell Rep. Feb. 1985;4(1):4-6.
Clough and Bent, (1998). Floral dip: A simplified method for Agrobacterium-mediated transformation of *Arabidopsis thaliana*. Plant J. Dec. 1998;16(6):735-743.
Colombier et al., Interstrand cross-linking reaction in triplexes containing a monofunctional transplatin-adduct. Nucleic Acids Res. Nov. 15, 1996;24(22):4519-4524.
Coumans et al., Plant development from isolated microspores of *Zea mays* L. Plant Cell Rep. Mar. 1989;7(8):618-621.
Datta et al., Embryogenesis and plant regeneration from microspores of both 'Indica' and 'Japonica' rice (*Oryza sativa*). Plant Sci. 1990;67:83-88.
Dhir et al., Regeneration of fertile plants from protoplasts of soybean (*Glycine max* L. Merr.); genotypic differences in culture response. Plant Cell Rep. Jun. 1992;11(5-6):285-289.
Fennell and Hauptman, Electroporation and PEG delivery of DNA into maize microspores. Plant Cell Rep. Oct. 1992;11(11):567-570.
Frame et al., Production of fertile transgenic maize plants by silicon carbide whisker-mediated transformation. Plant J. 1994;6(6):941-948.
Fujikawa and Kato, Split luciferase complementation assay to study protein-protein interactions in *Arabidopsis* protoplasts. Plant J. Oct. 2007;52(1):185-195.
Gallois et al., Electroporation of Tobacco Leaf Protoplasts Using Plasmid DNA or Total Genomic DNA. Methods Mol Biol. 1995;55:89-107.
Henikoff and Henikoff, Amino acid substitution matrices from protein blocks. Proc Natl Acad Sci U S A. Nov. 15, 1992;89(22):10915-10919.

(56) References Cited

OTHER PUBLICATIONS

Jardinaud et al., Transient GUS gene expression in *Brassica napus* electroporated microspores. Plant Sci. 1993;93(1-2):177-184.
Kane et al., Specific cleavage of a DNA triple helix by Fell. bleomycin. Biochemistry. Dec. 26, 1995,34(51):16715-16724.
Karlin and Altschul, Applications and statistics for multiple high-scoring segments in molecular sequences. Proc Natl Acad Sci U S A. Jun. 15, 1993;90(12):5873-5787.
Kartha et al., In vitro Plant Formation from Stem Explants of Rape (*Brassica napus* cv. Zephyr). Physiol Plant 1974;31(3):217-220.
Kipp et al., Gene-Targeting in Plants via Site-Directed Mutagenesis. Methods Mol Biol. 2000;133:213-221.
Komatsuda et al., Genotype X Sucrose Interactions for Somatic Embryogenesis in Soybeans. Crop Sci. 1991;31(2):333-337.
Komatsuda et al., Maturation and germination of somatic embryos as affected by sucrose and plant growth regulators in soybeans *Glycine gracilis* Skvortz and *Glycine max* (L.) Merr. Plant Cell, Tissue and Organ Culture, 1992;28(1):103-113.
Lukhtanov et al., Minor Groove DNA Alkylation Directed by Major Groove Triplex Forming Oligodeoxyribonucleotides. Nucleic Acids Res. Dec. 15, 1997;25(24):5077-5084.
Maheshwari et al., Haploids from pollen grains—retrospect and prospect. Amer J Bot. 1982;69: 865-879.
Mathur et al., A simple method for isolation, liquid culture, transformation and regeneration of *Arabidopsis thaliana* protoplasts. Plant Cell Rep. Jan. 1995;14(4):221-226.
Meyers and Miller, Optimal alignments in linear space. Comput Appl Biosci. Mar. 1988;4(1):11-17.
Narasimhulu and Chopra, Species Specific Shoot Regeneration Response of Cotyledonary Explants of *Brassicas*. Plant Cell Rep. Mar. 1988;7(2):104-106.
Needleman and Wunsch, A general method applicable to the search for similarities in the amino acid sequence of two proteins. J Mol Biol. Mar. 1970,48(3):443-453.
Nunez et al., Long-Range Guanine Oxidation in DNA Restriction Fragments by a Triplex-Directed Naphthalene Diimide Intercalator. Biochemistry. May 23, 2000;39(20):6190-6199.
Pandey et al., Plant Regeneration from Leaf and Hypocotyl Explants of Glycine wightii (W. and A.) Verdc. var. longicauda. Japan J. Breed. 1992;42:1-5.
Pearson and Lipman, Improved tools for biological sequence comparison. Proc Natl Acad Sci U S A. Apr. 1988;85(8):2444-2448.
Schaeffer, Role of Microspores and Anther Culture in Advancing Technologies. Adv in Cell Culture 1989;7:161-182.
Sergeyev et al., Catalytic site-specific cleavage of a DNA-target by an oligonucleotide carrying bleomycin A5. Nucleic Acids Res. Nov. 11, 1995;23(21):4400-4406.
Shetty et al., Stimulation of in vitro shoot organogenesis in Glycine max(Merrill.) by allantoin and amides. Plant Science 1992;81:245-251.
Smith and Waterman, Comparison of Biosequences. Adv Appl Math. Dec. 1981;2(4):482-489.
Stephens et al., Agronomic Evaluation of Tissue-Culture-Derived Soybean Plants. Theor Appl Genet. Oct. 1991;82(5):633-635.
Swanson et al., Efficient isolation of microspores and the production of microspore-derived embryos from *Brassica napus*. Plant Cell Rep. Apr. 1987;6(2):94-97.
Swanson, Microspore Culture in *Brassica*. Methods Mol Biol. 1990;6:159-169.
Thompson et al., CLUSTAL W: improving the sensitivity of progressive multiple sequence alignment through sequence weighting, position-specific gap penalties and weight matrix choice. Nucleic Acids Res. Nov. 11, 1994;22(22):4673-4680.

Zhang et al., Transcription Activator-Like Effector Nucleases Enable Efficient Plant Genome Engineering 1[W][OA]. Plant Physiol. Jan. 2013;161(1):20-27.
Office Action issued by SIPO in Chinese Patent Application No. 2014800247089 dated Mar. 30, 2018—incl Engl lang transl (11 pages total).
Office Action issued by the JPO in Japanese Patent Application 2016-503169 dated Aug. 20, 2019—incl Engl lang transl.
Gabsalilow et al., Site- and strand-specific nicking of DNA by fusion proteins derived from MutH and I-Scel or TALE repeats. Nucleic Acids Res. Apr. 2013;41(7):e83 (pp. 1-11).
Kim et al., Precision genome engineering with programmable DNA-nicking enzymes. Genome Res. Jul. 2012;22(7):1327-1333.
Sugiura, DNA Cleavage Activity and Metal Complexes of Bleomycin Antibiotics. Organic Synthesis Chemistry, 1981;39(11):1097-1104—Engl lang transl abstract only.
Office Action issued by the Brazilian Patent Office in Brazilian Patent Application BR 112015022848-8 dated Nov. 5, 2019.
Office Action issued by the JPO in Japanese Patent Application 2016-503169 dated Sep. 18, 2018—incl Engl lang transl (10 pages total).
Office Action issued by the EPO in European Patent Application No. 14763072.7 dated Apr. 20, 2018 (6 pages).
Dong et al., 0ligonucleotide-directed gene repair in wheat using a transient plasmid gene repair assay system. Plant Cell Rep. May 2006;25(5):457-465.
Office Action issued by the Israeli Patent Office ("ILPO") in Israeli Patent Application No. 241145 dated Aug. 9, 2018—incl Engl lang transl (8 pages total).
Lippincott-Schwartz and Patterson, "Development and Use of Fluorescent Protein Markers in Living Cells", Science, Apr. 4, 2003;300(5616):87-91.
Strouse et al., "Combinatorial gene editing in mammalian cells using ssODNs and TALENs", Sci. Rep. 4, 3791; DOI:10.1038/srep03791 (2014).
First Exam Report issued by the NZIPO in New Zealand Patent Application 711146 dated Jul. 31, 2020.
First Exam Report issued by the NZIPO in New Zealand Patent Application 751586 dated Jul. 31, 2020.
First Exam Report issued by the NZIPO in New Zealand Patent Application 751592 dated Jul. 31, 2020.
Office Action issued by the CNIPA in PRC Patent Application 2014800247089 dated Aug. 4, 2020—incl Engl lang transl.
Friedmann et al., Advances in Genetics, vol. 80. Elsevier,○c 2012, pp. 63-69—entire document provided (pp. 1-161).
Office Action issued by EAPO in Eurasian Patent Application 201591447/28 dated Oct. 23, 2020—incl Engl lang transl.
Renaud et al., "Improved Genome Editing Efficiency and Flexibility Using Modified Oligonucleotides with TALEN and CRISPR-Cas9 Nucleases", Cell Reports, 2016, 14, 2263-2272.
Rozov et al., "The Problem of the Low Rates of CRISPR/Cas9-Mediated Knock-ins in Plants: Approaches and Solutions", International Journal of Molecular Sciences, 2019, 20, 3371; doi:10.3390/ijms20133371.
Office Action issued by New Zealand IP Office in New Zealand Patent Application 711146 dated Apr. 6, 2021.
Moutinho et al., Antisense perturbation of protein function in living pollen tubes. Sex Plant Reprod. 2001;14:101-104.
Office Action issued by the Israeli Patent Office in Israeli Patent Application No. 241145 dated Nov. 23, 2021—incl Engl lang summary (10 pages total).
Cai et al., Targeted transgene integration in plant cells using designed zinc finger nucleases. Plant Mol Biol. Apr. 2009,69(6):699-709.

\* cited by examiner

CTTCATGTGGTCGGGGTAGCGGCTGAAGCACTGCACGCCGTGGGTGAAGGTGGTCACGAGGGTGGGCCAGGGCACGGG

GAAGTACACCAGCCCCATCGCCGACTTCGTGACGTGCGGACCACTTCCACCAGTGCTCCCACCCGGTCCCGTGCCC

K  M  H  D  P  Y  R  S  F  C  Q  V  G  H  T  F  T  T  V  L  T  P  W  P  V  P

SEQUENCE LISTING

<160> NUMBER OF SEQ ID NOS: 7

<210> SEQ ID NO 1
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
vccctcgtga ccaccttcac ctacggcgtg cagtgcttca gch                          43

<210> SEQ ID NO 2
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
vgctgaagca ctgcacgccg taggtgaagg tggtcacgag ggh                          43

<210> SEQ ID NO 3
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
vccctcgtga ccaccttcac ccacggcgtg cagtgcttca gch                          43

<210> SEQ ID NO 4
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
vgctgaagca ctgcacgccg tgggtgaagg tggtcacgag ggh                          43

<210> SEQ ID NO 5
<211> LENGTH: 78
<212> TYPE: DNA

```
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(78)

<400> SEQUENCE: 5 ccc gtg ccc tgg ccc acc ctc gtg acc acc ttc acc cac ggc gtg cag        48
Pro Val Pro Trp Pro Thr Leu Val Thr Thr Phe Thr His Gly Val Gln
1               5                   10                  15 tgc ttc agc cgc tac ccc gac cac atg aag                                78
Cys Phe Ser Arg Tyr Pro Asp His Met Lys
                20                  25

<210> SEQ ID NO 6
<211> LENGTH: 26
<212> TYPE: PRT
<213> ORGANISM: Artificial Sequence
<220> FEATURE:
<223> OTHER INFORMATION: Synthetic Peptide

<400> SEQUENCE: 6

Pro Val Pro Trp Pro Thr Leu Val Thr Thr Phe Thr His Gly Val Gln
1               5                   10                  15

Cys Phe Ser Arg Tyr Pro Asp His Met Lys
                20                  25

<210> SEQ ID NO 7
<211> LENGTH: 78
<212> TYPE: DNA
<213> ORGANISM: Artificial Sequence
<220> FEATURE:
<223> OTHER INFORMATION: Synthetic oligonucleotide

<400> SEQUENCE: 7
cttcatgtgg tcggggtagc ggctgaagca ctgcacgccg tgggtgaagg tggtcacgag       60
ggtgggccag ggcacggg                                                    78
```

US 11,434,494 B2

TARGETED GENE MODIFICATION USING OLIGONUCLEOTIDE-MEDIATED GENE REPAIR

The present invention is filed under 35 U.S.C. § 371 as the U.S. national phase of International Application No. PCT/US2014/029621, filed Mar. 14, 2014, which designated the United States and claims priority to U.S. Provisional Patent Application No. 61/801,320 filed Mar. 15, 2013, each of which is hereby incorporated by reference in its entirety including all tables, figures, and claims.

SEQUENCE LISTING

The instant application contains a Sequence Listing which has been submitted in ASCII format via EFS-Web and is hereby incorporated by reference in its entirety. Said ASCII copy, created on Sep. 15, 2015, is named CIBUS026US_SeqListing.txt and is 3 kilobytes in size.

FIELD OF THE INVENTION

This invention generally relates to novel methods to improve the efficiency of the targeting of modifications to specific locations in genomic or other nucleotide sequences. Additionally, this invention relates to target DNA that has been modified, mutated or marked by the approaches disclosed herein. The invention also relates to cells, tissue, and organisms which have been modified by the invention's methods.

BACKGROUND OF THE INVENTION

DNA double-strand breaking (DSB) enhances homologous recombination in living cells and has been exploited for targeted genome editing through use of engineered endonucleases. The key component of the engineered nucleases is the DNA recognition domain that is capable of directing the nuclease to the target site of genome for a genomic DNA double strand break. The cellular DSB repair due to non-homologous end-joining (NHEJ) results in mutagenic deletions/insertions of a target gene. Alternately, the DSB can stimulate homologous recombination between the endogenous target locus and an exogenously introduced homologous DNA fragment with desired genetic information, a process called gene targeting.

The most promising method involving gene or genome editing is the custom-designed zinc finger nucleases (ZFN), a type of hybrid enzyme consisting of DNA binding domains of zinc finger proteins and the FokI nuclease domain (FN). The ZFN technology primarily involves the use of hybrid proteins derived from the DNA binding domains of zinc finger (ZF) proteins and the nonspecific cleavage domain of the endonuclease FokI. The ZFs can be assembled as modules that are custom-designed to recognize selected DNA sequences following binding at the preselected site, a DSB is produced by the action of cleavage domain of FokI.

The FokI endonuclease was first isolated from the bacterium *Flavobacterium okeanokoites*. This type IIS nuclease consists of two separate domains, the N-terminal DNA binding domain and C-terminal DNA cleavage domain. The DNA binding domain functions for recognition of a non-palindromic sequence 5'-GGATG-3'/5'-CATCC-3' while the catalytic domain cleaves double-stranded DNA non-specifically at a fixed distance of 9 and 13 nucleotides downstream of the recognition site. FokI exists as an inactive monomer in solution and becomes an active dimmer following the binding to its target DNA and in the presence of some divalent metals. As a functional complex, two molecules of FokI each binding to a double stranded DNA molecule dimerize through the DNA catalytic domain for the effective cleavage of DNA double strands.

In a similar fashion, nucleases can also be made by using other proteins/domains if they are capable of specific DNA recognition. TAL effectors belong to a large group of bacterial proteins that exist in various strains of *Xanthomonas* and are translocated into host cells by a type III secretion system, so called type III effectors. Once in host cells, some TAL effectors have been found to transcriptionally activate their corresponding host target genes either for strain virulence (ability to cause disease) or avirulence (capacity to trigger host resistance responses) dependent on the host genetic context. Each effector contains the functional nuclear localization motifs and a potent transcription activation domain that are characteristic of eukaryotic transcription activator. And each effector also contains a central repetitive region consisting of varying numbers of repeat units of 34 amino acids, and the repeat region as DNA binding domain determines the biological specificity of each effector.

Zhang et al., Plant Physiol. 161: 20-27, 2013, which is hereby incorporated by reference in its entirety, discloses the use of TALENs—transcriptional activator-like effector nucleases—which are engineered endonucleases based on the combination of a TAL effector-like DNA binding domain with a catalytic domain of FokI. By engineering of the DNA binding domain, these TALENs reportedly can be easily designed to recognize specific DNA binding domains. Using tobacco protoplasts as a model system, TALEN activity was assessed using a single strand annealing polynucleotide reporter comprising a yellow fluorescent protein coding sequence linked to a TALEN recognition site. This reporter system was delivered to protoplasts, and a cleavage-and-repair event could be measured by expression of functional YFP.

SUMMARY OF THE INVENTION

In a first aspect, the invention relates to methods for introducing a gene repair oligonucleobase (GRON)-mediated mutation into a target deoxyribonucleic acid (DNA) sequence in a plant cell. The methods comprise, inter alia, culturing the plant cell under conditions that increase one or more cellular DNA repair processes prior to, and/or coincident with, delivery of a GRON into the plant cell In certain embodiments, the conditions that increase one or more cellular DNA repair processes comprise one or more of: introduction of one or more sites into the GRON or into the plant cell DNA that are targets for base excision repair, introduction of one or more sites into the GRON or into the plant cell DNA that are targets for non-homologous end joining, introduction of one or more sites into the GRON or into the plant cell DNA that are targets for microhomology-mediated end joining, introduction of one or more sites into the GRON or into the plant cell DNA that are targets for homologous recombination, and introduction of one or more sites into the GRON or into the plant cell DNA that are targets for pushing repair.

In certain embodiments, the target deoxyribonucleic acid (DNA) sequence is within the plant cell genome. The plant cell may be non-transgenic or transgenic, and the target DNA sequence may be a transgene or an endogenous gene of the plant cell.

In certain embodiments, the conditions that increase one or more cellular DNA repair processes comprise introducing one or more compounds which induce single or double DNA strand breaks into the plant cell prior to or coincident with delivering the GRON into the plant cell. Exemplary compounds are described hereinafter.

The methods and compositions described herein are applicable to plants generally. By way of example only, a plant species may be selected from the group consisting of canola, sunflower, corn, tobacco, sugar beet, cotton, maize, wheat, barley, rice, alfafa, barley, sorghum, tomato, mango, peach, apple, pear, strawberry, banana, melon, potato, carrot, lettuce, onion, soy bean, soya spp, sugar cane, pea, chickpea, field pea, faba bean, lentils, turnip, rutabaga, brussel sprouts, lupin, cauliflower, kale, field beans, poplar, pine, eucalyptus, grape, citrus, triticale, alfalfa, rye, oats, turf and forage grasses, flax, oilseed rape, mustard, cucumber, morning glory, balsam, pepper, eggplant, marigold, lotus, cabbage, daisy, carnation, tulip, iris, and lily. These may also apply in whole or in part to all other biological systems including but not limited to bacteria, fungi and mammalian cells and even their organelles (e.g., mitochondria and chloroplasts).

In certain embodiments, the methods further comprise regenerating a plant having a mutation introduced by the GRON from the plant cell, and may comprise collecting seeds from the plant.

In related aspects, the present invention relates to plant cells comprising a genomic modification introduced by a GRON according to the methods described herein, a plant comprising a genomic modification introduced by a GRON according to the methods described herein, or a seed comprising a genomic modification introduced by a GRON according to the methods described herein.

Other embodiments of the invention will be apparent from the following detailed description, exemplary embodiments, and claims.

DETAILED DESCRIPTION OF THE DRAWINGS

DETAILED DESCRIPTION OF THE INVENTION

Definitions

Figure 1:
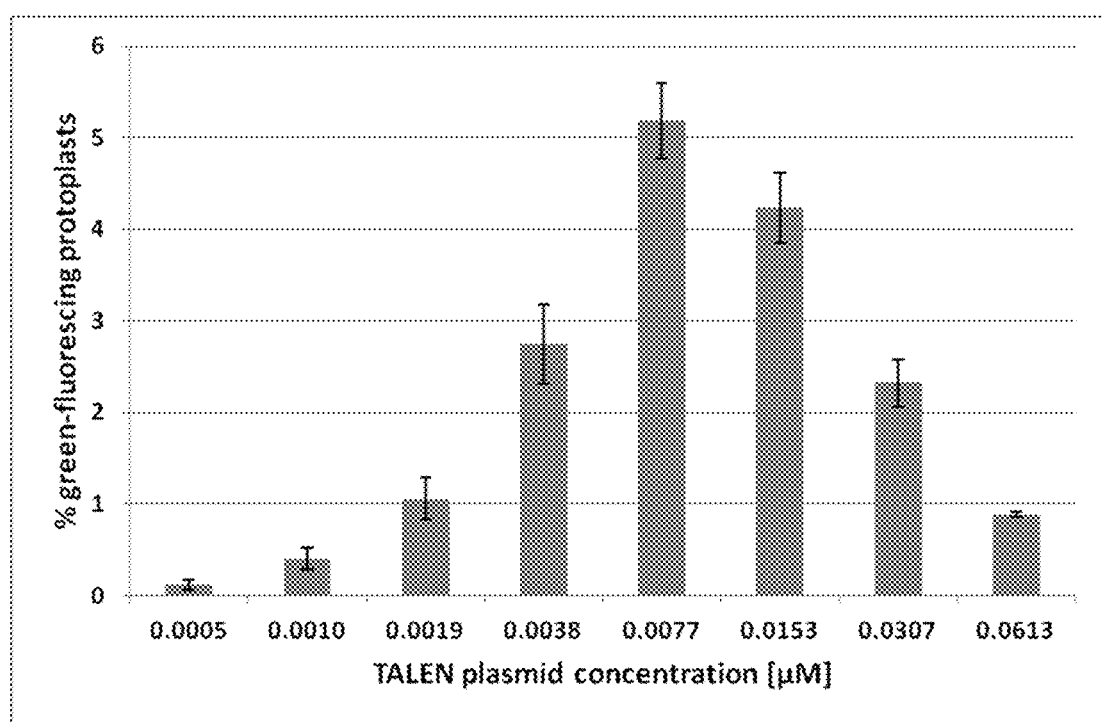
FIG. 1 depicts the effect of TALEN concentration on GRON targeting of a GFP to BFP mutation in an *Arabidopsis* protoplast model.
Figure 2:
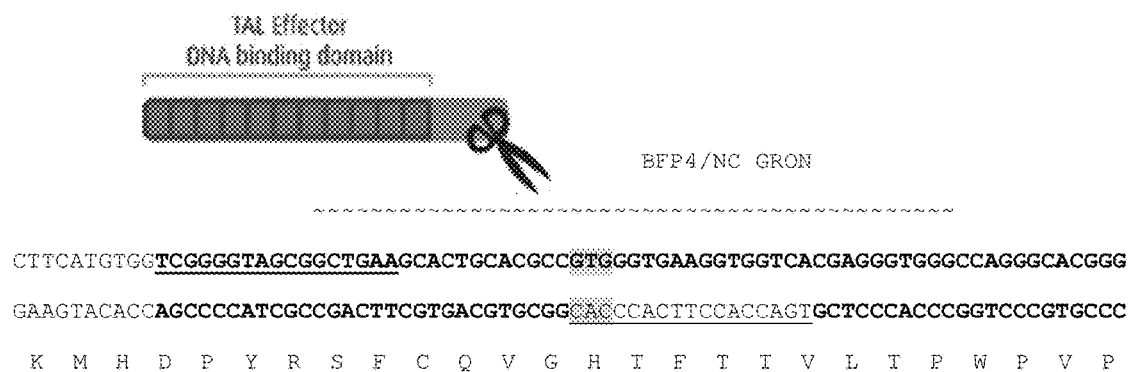
FIG. 2 depicts the design of a TALEN for use in targeting a BFP to GFP mutation as described in the Examples. Sequences depicted are: CTTCATGTGGTCGGGGTA-GCGGCTGAAGCACTGCACGCCGTGGGTGAAGGT-GGTCA CGAGGGTGGGCCAGGGCACGGG (SEQ ID NO: 7; 5'-3') GAAGTACACCAGCCCCATCGCCGAC-TTCGTGACGTGCGGCACCCACTTCCACCAGTG CT-CCCACCCGGTCCCGTGCCC (SEQ ID NO: 5; 3'-5') KM-HDPYRSFCQVGHTFTTVLTPWPVP (SEQ ID NO: 6; 3'-5').
Figure 2:

The invention is to be understood in accordance with the following definitions.

An oligonucleobase is a polymer of nucleobases, which polymer can hybridize by Watson-Crick base pairing to a DNA having the complementary sequence.

Nucleobases comprise a base, which is a purine, pyrimidine, or a derivative or analog thereof. Nucleobases include peptide nucleobases, the subunits of peptide nucleic acids, and morpholine nucleobases as well as nucleosides and nucleotides. Nucleosides are nucleobases that contain a pentosefuranosyl moiety, e.g., an optionally substituted riboside or 2'-deoxyriboside. Nucleosides can be linked by one of several linkage moieties, which may or may not contain a phosphorus. Nucleosides that are linked by unsubstituted phosphodiester linkages are termed nucleotides.

An oligonucleobase chain has a single 5' and 3' terminus, which are the ultimate nucleobases of the polymer. A particular oligonucleobase chain can contain nucleobases of all types. An oligonucleobase compound is a compound comprising one or more oligonucleobase chains that are complementary and hybridized by Watson-Crick base pairing. Nucleobases are either deoxyribo-type or ribo-type. Ribo-type nucleobases are pentosefuranosyl containing nucleobases wherein the 2' carbon is a methylene substituted with a hydroxyl, alkyloxy or halogen. Deoxyribo-type nucleobases are nucleobases other than ribo-type nucleobases and include all nucleobases that do not contain a pentosefuranosyl moiety.

An oligonucleobase strand generically includes both oligonucleobase chains and segments or regions of oligonucleobase chains. An oligonucleobase strand has a 3' end and a 5' end. When a oligonucleobase strand is coextensive with a chain, the 3' and 5' ends of the strand are also 3' and 5' termini of the chain.

According to the present invention plant organs include, but are not limited to, leaves, stems, roots, vegetative buds, floral buds, meristems, embryos, cotyledons, endosperm, sepals, petals, pistils, carpels, stamens, anthers, microspores, pollen, pollen tubes, ovules, ovaries and fruits, or sections, slices or discs taken therefrom. Plant tissues include, but are not limited to, callus tissues, ground tissues, vascular tissues, storage tissues, meristematic tissues, leaf tissues, shoot tissues, root tissues, gall tissues, plant tumor tissues, and reproductive tissues. Plant cells include, but are not limited to, isolated cells with cell walls, variously sized aggregates thereof, and protoplasts.

Two polynucleotides or polypeptides are identical if the sequence of nucleotides or amino acid residues, respectively, in the two sequences is the same when aligned for maximum correspondence as described below. The terms "identical" or "percent identity," in the context of two or more nucleic acids or polypeptide sequences, refer to two or more sequences or subsequences that are the same or have a specified percentage of amino acid residues or nucleotides that are the same, when compared and aligned for maximum correspondence over a comparison window, as measured using one of the following sequence comparison algorithms or by manual alignment and visual inspection. For polypeptides where sequences differ in conservative substitutions, the percent sequence identity may be adjusted upwards to correct for the conservative nature of the substitution. Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a 'score of zero, a conservative substitution is given a score between zero and 1. The scoring of conservative substitutions is calculated according to, e.g., the algorithm of Meyers & Miller, Computer Applic. Biol. Sci. 4: 11-17 (1988) e.g., as implemented in the program PC/GENE (Intelligenetics, Mountain View, Calif., USA).

The phrases "substantially identical," and "percent identity" in the context of two nucleic acids or polypeptides, refer to sequences or subsequences that have at least 50%, advantageously 60%, preferably 70%, more preferably 80%, and most preferably 90-95% nucleotide or amino acid residue identity when aligned for maximum correspondence over a comparison window as measured using one of the following sequence comparison algorithms or by manual alignment and visual inspection. This definition also refers to the complement of a test sequence, which has substantial sequence or subsequence complementarity when the test sequence has substantial identity to a reference sequence.

One of skill in the art will recognize that two polypeptides can also be "substantially identical" if the two polypeptides are immunologically similar. Thus, overall protein structure may be similar while the primary structure of the two polypeptides display significant variation. Therefore a method to measure whether two polypeptides are substantially identical involves measuring the binding of monoclonal or polyclonal antibodies to each polypeptide. Two polypeptides are substantially identical if the antibodies specific for a first polypeptide bind to a second polypeptide with an affinity of at least one third of the affinity for the first polypeptide. For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, 0.4dv. Appl. Math. 2:482 (I 98 I), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), by software for alignments such as VECTOR NTI Version #6 by InforMax, Inc. MD, USA, by the procedures described in ClustalW, Thompson, J. D., Higgins, D. G. and Gibson, T. J. (1994) CLUSTALW: improving the sensitivity of progressive multiple sequence alignment through sequence weighting, position—specific gap penalties and weight matrix choice. Nucleic Acids Research, 22:4673-4680 or by visual inspection (see generally, Protocols in Molecular Biology, F. M. Ausubel et al., eds., Current Protocols, a joint venture between Greene Publishing Associates, Inc. and John Wiley & Sons, Inc., (1995 Supplement) (Ausubel)).

Examples of algorithms that are suitable for determining percent sequence identity and sequence similarity are the BLAST and BLAST 2.0 algorithms, which are described in Altschul et al. (1990) J. Mol. Biol. 215: 403-410 and Altschul et al. (1977) Nucleic Acids Res. 25: 33 89-3402, respectively. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word length (W) of 11, an expectation (E) of 10, M=5, N=−4, and a comparison of both strands. For amino acid sequences, the BLASTP program uses as defaults a word length (W) of 3, an expectation (E) of 10, and the BLOSUM62 scoring matrix (see Henikoff & Henikoff, Proc. Natl. Acad. Sci. USA 89:10915 (1989)). In addition to calculating percent sequence identity, the BLAST algorithm also performs a statistical analysis of the similarity between two sequences (see, e.g., Karlin & Altschul, Proc. Nat'l. Acad. Sci. USA 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

Strand Breakage

Inclusion of compounds which induce single or double strand breaks, either into the oligonucleotide or together with the oligonucleotide, generates a lesion which is repaired by non-homologous end joining (NHEJ), microhomology-mediated end joining (MMEJ), and homologous recombination. By way of example, the bleomycin family of antibiotics, zinc finger nucleasess, FokI (or any type IIS class of restriction enzyme) and other nucleases may be covalently coupled to the 3' or 5' end of repair oligonucleotides, in order to introduce double strand breaks in the vicinity of the site targeted for conversion by the repair oligonucleotide. The bleomycin family of antibiotics are DNA cleaving glycopeptides include bleomycin, zeocin, phleomycin, tallysomycin, pepleomycin and others.

The invention's methods are not limited to the nature or type of DNA-modifying reagent which is used. For example, such DNA-modifying reagents release radicals which result in DNA strand breakage. Alternatively, the reagents alkylate DNA to form adducts which would block replication and transcription. In another alternative, the reagents generate crosslinks or molecules that inhibit cellular enzymes leading to strand breaks. Examples of DNA-modifying reagents which have been linked to oligonucleotides to form TFOs include, but are not limited to, indolocarbazoles, napthalene diimide (NDI), transplatin, bleomycin, analogues of cyclopropapyrroloindole, and phenanthodihydrodioxins. In particular, indolocarbazoles are topoisomerase I inhibitors. Inhibition of these enzymes results in strand breaks and DNA protein adduct formation [Arimondo et al., Bioorganic and Medicinal Chem. 8, 777, 2000]. NDI is a photooxidant that can oxidize guanines which could cause mutations at sites of guanine residues [Nunez, et al., Biochemistry, 39, 6190, 2000]. Transplatin has been shown to react with DNA in a triplex target when the TFO is linked to the reagent. This reaction causes the formation of DNA adducts which would be mutagenic [Columbier, et al., Nucleic Acids Research, 24: 4519, 1996]. Bleomycin is a DNA breaker, widely used as a radiation mimetic. It has been linked to oligonucleotides and shown to be active as a breaker in that format [Sergeyev, Nucleic Acids Research 23, 4400, 1995; Kane, et al., Biochemistry, 34, 16715, 1995]. Analogues of cyclopropapyrroloindole have been linked to TFOs and shown to alkylate DNA in a triplex target sequence. The alkylated DNA would then contain chemical adducts which would be mutagenic [Lukhtanov, et al., Nucleic Acids Research, 25, 5077, 1997]. Phenanthodihydrodioxins are masked quinones that release radical species upon photoactivation. They have been linked to TFOs and have been shown to introduce breaks into duplex DNA on photoactivation [Bendinskas et al., Bioconjugate Chem. 9, 555, 1998].

One strategy for producing targeted gene disruption is through the generation of single strand or double strand DNA breaks caused by site-specific endonucleases. Endonucleases are most often used for targeted gene disruption in organisms that have traditionally been refractive to more conventional gene targeting methods, such as algae, plants, and large animal models, including humans. For example, there are currently human clinical trials underway involving zinc finger nucleases for the treatment and prevention of HIV infection. Additionally, endonuclease engineering is currently being used in attempts to disrupt genes that produce undesirable phenotypes in crops.

The homing endonucleases, also known as meganucleases, are sequence specific endonucleases that generate double strand breaks in genomic DNA with a high degree of specificity due to their large (e.g., >14 bp) cleavage sites. While the specificity of the homing endonucleases for their target sites allows for precise targeting of the induced DNA breaks, homing endonuclease cleavage sites are rare and the probability of finding a naturally occurring cleavage site in a targeted gene is low.

Engineered homing endonucleases are generated by modifying the specificity of existing homing endonucleases. In one approach, variations are introduced in the amino acid sequence of naturally occurring homing endonucleases and then the resultant engineered homing endonucleases are screened to select functional proteins which cleave a targeted binding site. In another approach, chimeric homing endonucleases are engineered by combining the recognition sites of two different homing endonucleases to create a new recognition site composed of a half-site of each homing endonuclease.

One class of artificial endonucleases is the zinc finger endonucleases. Zinc finger endonucleases combine a non-specific cleavage domain, typically that of FokI endonuclease, with zinc finger protein domains that are engineered to bind to specific DNA sequences. The modular structure of the zinc finger endonucleases makes them a versatile platform for delivering site-specific double-strand breaks to the genome. One limitation of the zinc finger endonucleases is that low specificity for a target site or the presence of multiple target sites in a genome can result in off-target cleavage events. As FokI endonuclease cleaves as a dimer, one strategy to prevent off-target cleavage events has been to design zinc finger domains that bind at adjacent 9 base pair sites.

TALENs are targetable nucleases are used to induce single- and double-strand breaks into specific DNA sites, which are then repaired by mechanisms that can be exploited to create sequence alterations at the cleavage site.

The fundamental building block that is used to engineer the DNA-binding region of TALENs is a highly conserved repeat domain derived from naturally occurring TALEs encoded by *Xanthomonas* spp. proteobacteria. DNA binding by a TALEN is mediated by arrays of highly conserved 33-35 amino acid repeats that are flanked by additional TALE-derived domains at the amino-terminal and carboxy-terminal ends of the repeats.

These TALE repeats specifically bind to a single base of DNA, the identity of which is determined by two hypervariable residues typically found at positions 12 and 13 of the repeat, with the number of repeats in an array corresponded to the length of the desired target nucleic acid, the identity of the repeat selected to match the target nucleic acid sequence. The target nucleic acid is preferably between 15 and 20 base pairs in order to maximize selectivity of the target site. Cleavage of the target nucleic acid typically occurs within 50 base pairs of TALEN binding. Computer programs for TALEN recognition site design have been described in the art. See, e.g., Cermak et al., Nucleic Acids Res. 2011 July; 39(12): e82.

Once designed to match the desired target sequence, TALENS can be expressed recombinantly and introduced into protoplasts as exogenous proteins, or expressed from a plasmid within the protoplast.

GRON Structure and Introduction into Plant Cells

The recombinagenic oligonucleobase can be introduced into a plant cell using any method commonly used in the art, including but not limited to, microcarriers (biolistic delivery), microfibers (whiskers), electroporation, direct DNA uptake and microinjection. Illustrative examples of a recombinagenic oligonucleobase are described in FIGS. 4-13.

The invention can be practiced with recombinagenic oligonucleobases having the conformations and chemistries described in the Kmiec I and Kmiec II patents which are incorporated herein by reference. Kmiec I teaches a method for introducing specific genetic alterations into a target gene. The recombinagenic oligonucleobases in Kmiec I and/or Kmiec II contain two complementary strands, one of which contains at least one segment of RNA-type nucleotides (an "RNA segment") that are base paired to DNA-type nucleotides of the other strand.

Kmiec II discloses that purine and pyrimidine base-containing non-nucleotides can be substituted for nucleotides. U.S. Pat. Nos. 5,756,325; 5,871,984; 5,760,012; 5,888,983; 5,795,972; 5,780,296; 5,945,339; 6,004,804; and 6,010,907 and in International Patent No. PCT/US00/23457; and in International Patent Publication Nos. WO 98/49350; WO 99/07865; WO 99/58723; WO 99/58702; WO 99/40789; U.S. Pat. No. 6,870,075; and US Published Patent Application 20030084473, which are each hereby incorporated in their entirety, disclose additional recombinagenic molecules that can be used for the present invention. The term "recombinagenic oligonucleobase" is used herein to denote the molecules that can be used in the methods of the present invention and include mixed duplex oligonucleotides, non-nucleotide containing molecules taught in Kmiec II, single stranded oligodeoxynucleotides and other recombinagenic molecules taught in the above noted patents and patent publications.

In one embodiment, the recombinagenic oligonucleobase is a mixed duplex oligonucleotide in which the RNA-type nucleotides of the mixed duplex oligonucleotide are made RNase resistant by replacing the 2'-hydroxyl with a fluoro, chloro or bromo functionality or by placing a substituent on the 2'-O. Suitable substituents include the substituents taught by the Kmiec II. Alternative substituents include the substituents taught by U.S. Pat. No. 5,334,711 (Sproat) and the substituents taught by patent publications EP 629 387 and EP 679 657 (collectively, the Martin Applications), which are incorporated herein by reference. As used herein, a 2'-fluoro, chloro or bromo derivative of a ribonucleotide or a ribonucleotide having a 2'-OH substituted with a substituent described in the Martin Applications or Sproat is termed a "2'-Substituted Ribonucleotide." As used herein the term "RNA-type nucleotide" means a 2'-hydroxyl or 2'-Substituted Nucleotide that is linked to other nucleotides of a mixed duplex oligonucleotide by an unsubstituted phosphodiester linkage or any of the non-natural linkages taught by Kmiec I or Kmiec II. As used herein the term "deoxyribo-type nucleotide" means a nucleotide having a 2'-H, which can be linked to other nucleotides of a MDON by an unsubstituted phosphodiester linkage or any of the non-natural linkages taught by Kmiec I or Kmiec II.

In one embodiment of the present invention, the recombinagenic oligonucleobase is a mixed duplex oligonucleotide that is linked solely by unsubstituted phosphodiester bonds. In alternative embodiments, the linkage is by substituted phosphodiesters, phosphodiester derivatives and non-phosphorus-based linkages as taught by Kmiec II. In yet another embodiment, each RNA-type nucleotide in the mixed duplex oligonucleotide is a 2'-Substituted Nucleotide. Particularly preferred embodiments of 2'-Substituted Ribonucleotides are 2'-fluoro, 2'-methoxy, 2'-propyloxy, 2'-allyloxy, 2'-hydroxylethyloxy, 2'-methoxyethyloxy, 2'-fluoropropyloxy and 2'-trifluoropropyloxy substituted ribonucleotides. More preferred embodiments of 2'-Substituted Ribonucleotides are 2'-fluoro, 2'-methoxy, 2'-methoxyethyloxy, and 2'-allyloxy substituted nucleotides. In another embodiment the mixed duplex oligonucleotide is linked by unsubstituted phosphodiester bonds.

Although mixed duplex oligonucleotide having only a single type of 2'-substituted RNA-type nucleotide are more conveniently synthesized, the methods of the invention can be practiced with mixed duplex oligonucleotides having two or more types of RNA-type nucleotides. The function of an RNA segment may not be affected by an interruption caused by the introduction of a deoxynucleotide between two RNA-type trinucleotides, accordingly, the term RNA segment encompasses such an "interrupted RNA segment." An uninterrupted RNA segment is termed a contiguous RNA segment. In an alternative embodiment an RNA segment can contain alternating RNase-resistant and unsubstituted 2'-OH nucleotides. The mixed duplex oligonucleotides preferably have fewer than 100 nucleotides and more preferably fewer than 85 nucleotides, but more than 50 nucleotides. The first and second strands are Watson-Crick base paired. In one embodiment the strands of the mixed duplex oligonucleotide are covalently bonded by a linker, such as a single stranded hexa, penta or tetranucleotide so that the first and second strands are segments of a single oligonucleotide chain having a single 3' and a single 5' end. The 3' and 5' ends can be protected by the addition of a "hairpin cap" whereby the 3' and 5' terminal nucleotides are Watson-Crick paired to adjacent nucleotides. A second hairpin cap can, additionally, be placed at the junction between the first and second strands distant from the 3' and 5' ends, so that the Watson-Crick pairing between the first and second strands is stabilized.

The first and second strands contain two regions that are homologous with two fragments of the target ACCase gene, i.e., have the same sequence as the target gene. A homologous region contains the nucleotides of an RNA segment and may contain one or more DNA-type nucleotides of connecting DNA segment and may also contain DNA-type nucleotides that are not within the intervening DNA segment. The two regions of homology are separated by, and each is adjacent to, a region having a sequence that differs from the sequence of the target gene, termed a "heterologous region." The heterologous region can contain one, two or three mismatched nucleotides. The mismatched nucleotides can be contiguous or alternatively can be separated by one or two nucleotides that are homologous with the target gene. Alternatively, the heterologous region can also contain an insertion or one, two, three or of five or fewer nucleotides. Alternatively, the sequence of the mixed duplex oligonucleotide may differ from the sequence of the target gene only by the deletion of one, two, three, or five or fewer nucleotides from the mixed duplex oligonucleotide. The length and position of the heterologous region is, in this case, deemed to be the length of the deletion, even though no nucleotides of the mixed duplex oligonucleotide are within the heterologous region. The distance between the fragments of the target gene that are complementary to the two homologous regions is identically the length of the heterologous region when a substitution or substitutions is intended. When the heterologous region contains an insertion, the homologous regions are thereby separated in the mixed duplex oligonucleotide farther than their complementary homologous fragments are in the gene, and the converse is applicable when the heterologous region encodes a deletion.

The RNA segments of the mixed duplex oligonucleotides are each a part of a homologous region, i.e., a region that is identical in sequence to a fragment of the target gene, which segments together preferably contain at least 13 RNA-type nucleotides and preferably from 16 to 25 RNA-type nucleotides or yet more preferably 18-22 RNA-type nucleotides or most preferably 20 nucleotides. In one embodiment, RNA segments of the homology regions are separated by and adjacent to, i.e., "connected by" an intervening DNA segment. In one embodiment, each nucleotide of the heterologous region is a nucleotide of the intervening DNA segment. An intervening DNA segment that contains the heterologous region of a mixed duplex oligonucleotide is termed a "mutator segment."

The change to be introduced into the target gene is encoded by the heterologous region. The change to be introduced into the Agene may be a change in one or more bases of the gene sequence that changes the native amino acid in that position to the desired amino acid.

In another embodiment of the present invention, the recombinagenic oligonucleobase is a single stranded oligodeoxynucleotide mutational vector or SSOMV, which is disclosed in International Patent Application PCT/US00/23457, which is incorporated herein by reference in its entirety. The sequence of the SSOMV is based on the same principles as the mutational vectors described in U.S. Pat. Nos. 5,756,325; 5,871,984; 5,760,012; 5,888,983; 5,795,972; 5,780,296; 5,945,339; 6,004,804; and 6,010,907 and in International Publication Nos. WO 98/49350; WO 99/07865; WO 99/58723; WO 99/58702; WO 99/40789; U.S. Pat. No. 6,870,075; and US Published Patent Application 20030084473. The sequence of the SSOMV contains two regions that are homologous with the target sequence separated by a region that contains the desired genetic alteration termed the mutator region. The mutator region can have a sequence that is the same length as the sequence that separates the homologous regions in the target sequence, but having a different sequence. Such a mutator region will cause a substitution.

The nucleotides of the SSOMV are deoxyribonucleotides that are linked by unmodified phosphodiester bonds except that the 3' terminal and/or 5' terminal internucleotide linkage or alternatively the two 3' terminal and/or 5' terminal internucleotide linkages can be a phosphorothioate or phosphoamidate. As used herein an internucleotide linkage is the linkage between nucleotides of the SSOMV and does not include the linkage between the 3' end nucleotide or 5' end nucleotide and a blocking substituent, see supra. In a specific embodiment the length of the SSOMV is between 21 and 55 deoxynucleotides and the lengths of the homology regions are, accordingly, a total length of at least 20 deoxynucleotides and at least two homology regions should each have lengths of at least 8 deoxynucleotides.

The SSOMV can be designed to be complementary to either the coding or the non-coding strand of the target gene. When the desired mutation is a substitution of a single base, it is preferred that both the mutator nucleotides be a pyrimidine. To the extent that is consistent with achieving the desired functional result it is preferred that both the mutator nucleotide and the targeted nucleotide in the complementary strand be pyrimidines. Particularly preferred are SSOMV that encode transversion mutations, i.e., a C or T mutator nucleotide is mismatched, respectively, with a C or T nucleotide in the complementary strand.

In addition to the oligodeoxynucleotide the SSOMV can contain a 5' blocking substituent that is attached to the 5' terminal carbons through a linker. The chemistry of the linker is not critical other than its length, which should preferably be at least 6 atoms long and that the linker should be flexible. A variety of non-toxic substituents such as biotin, cholesterol or other steroids or a non-intercalating cationic fluorescent dye can be used. Particularly preferred as reagents to make SSOMV are the reagents sold as Cy3™ and Cy5™ by Glen Research, Sterling Va. (now GE Healthcare), which are blocked phosphoroamidites that upon incorporation into an oligonucleotide yield 3,3,3',3'-tetramethyl N,N'-isopropyl substituted indomonocarbocyanine and indodicarbocyanine dyes, respectively. Cy3 is the most preferred. When the indocarbocyanine is N-oxyalkyl substituted it can be conveniently linked to the 5' terminal of the oligodeoxynucleotide through as a phosphodiester with a 5' terminal phosphate. The chemistry of the dye linker between the dye and the oligodeoxynucleotide is not critical and is chosen for synthetic convenience. When the commercially available Cy3 phosphoramidite is used as directed the resulting 5' modification consists of a blocking substituent and linker together which are a N-hydroxypropyl, N'-phosphatidylpropyl 3,3,3',3'-tetramethyl indomonocarbocyanine.

In a preferred embodiment the indocarbocyanine dye is tetra substituted at the 3 and 3' positions of the indole rings. Without limitation as to theory these substitutions prevent the dye from being an intercalating dye. The identity of the substituents at these positions are not critical. The SSOMV can in addition have a 3' blocking substituent. Again the chemistry of the 3' blocking substituent is not critical.

In another preferred embodiment the recombinageneic oligonucleotide is a single-stranded oligodeoxynucleotide having a 3' end nucleotide, a 5' end nucleotide, having at least 25 deoxynucleotides and not more than 65 deoxynucleotides, and having a sequence comprising at least two regions each of at least 8 deoxynucleotides that are each, respectively, identical to at least two regions of the targeted chromosomal gene, which regions together are at least 24 nucleotides in length, and which regions are separated by at least one nucleotide in the sequence of the targeted chromosomal gene or in the sequence of the oligodeoxynucleotide or both such that the sequence of the oligodeoxynucleotide is not identical to the sequence of the targeted chromosomal gene. See U.S. Pat. No. 6,271,360 which is incorporated herein by reference.

Microcarriers and Microfibers

The use of metallic microcarriers (microspheres) for introducing large fragments of DNA into plant cells having cellulose cell walls by projectile penetration is well known to those skilled in the relevant art (henceforth biolistic delivery). U.S. Pat. Nos. 4,945,050; 5,100,792 and 5,204,253 describe general techniques for selecting microcarriers and devices for projecting them. U.S. Pat. Nos. 5,484,956 and 5,489,520 describe the preparation of fertile transgenic corn using microprojectile bombardment of corn callus tissue. The biolistic techniques are also used in transforming immature corn embryos.

Specific conditions for using microcarriers in the methods of the present invention are described in International Publication WO 99/07865. In an illustrative technique, ice cold microcarriers (60 mg/ml), mixed duplex oligonucleotide (60 mg/ml) 2.5 M $CaCl_2$) and 0.1 M spermidine are added in that order; the mixture is gently agitated, e.g., by vortexing, for 10 minutes and let stand at room temperature for 10 minutes, whereupon the microcarriers are diluted in 5 volumes of ethanol, centrifuged and resuspended in 100% ethanol. Good results can be obtained with a concentration in the adhering solution of 8-10 μg/μl microcarriers, 14-17 μg/ml mixed duplex oligonucleotide, 1.1-1.4 M CaC$_2$ and 18-22 mM spermidine. Optimal results were observed under the conditions of 8 μg/μl microcarriers, 16.5 μg/ml mixed duplex oligonucleotide, 1.3 M CaCl and 21 mM spermidine.

Recombinagenic oligonucleobases can also be introduced into plant cells for the practice of the present invention using microfibers to penetrate the cell wall and cell membrane. U.S. Pat. No. 5,302,523 to Coffee et al. describes the use of 30.times.0.5 μm and 10.times.0.3 μm silicon carbide fibers to facilitate transformation of suspension maize cultures of Black Mexican Sweet. Any mechanical technique that can be used to introduce DNA for transformation of a plant cell using microfibers can be used to deliver recombinagenic oligonucleobases for use in making the present ACCase mutants. An illustrative technique for microfiber delivery of a recombinagenic oligonucleobase is as follows: Sterile microfibers (2 μg) are suspended in 150 μl of plant culture medium containing about 10 μg of a mixed duplex oligonucleotide. A suspension culture is allowed to settle and equal volumes of packed cells and the sterile fiber/nucleotide suspension are vortexed for 10 minutes and plated. Selective media are applied immediately or with a delay of up to about 120 hours as is appropriate for the particular trait.

Electroporation

In an alternative embodiment, the recombinagenic oligonucleobases can be delivered to the plant cell by electroporation of a protoplast derived from a plant part according to techniques that are well-known to one of ordinary skill in the art. See, e.g., Gallois et al., 1996, in Methods in Molecular Biology 55:89-107, Humana Press, Totowa, N.J.; Kipp et al., 1999, in Methods in Molecular Biology 133:213-221, Humana Press, Totowa, N.J.

Recombinagenic oligonucleobases can also be introduced into microspores by electroporation. Upon release of the tetrad, the microspore is uninucleate and thin-walled. It begins to enlarge and develops a germpore before the exine forms. A microspore at this stage is potentially more amenable to transformation with exogenous DNA than other plant cells. In addition, microspore development can be altered in vitro to produce either haploid embryos or embryogenic callus that can be regenerated into plants (Coumans et al., Plant Cell Rep. 7:618-621, 1989; Datta et al., Plant Sci. 67:83-88, 1990; Maheshwari et al., Am. J Bot. 69:865-879, 1982; Schaeffer, Adv. In Cell Culture 7:161-182, 1989; Swanson et al., Plant Cell Rep. 6:94-97, 1987). Thus, transformed microspores can be regenerated directly into haploid plants or dihaploid fertile plants upon chromosome doubling by standard methods. See also co-pending application U.S. Ser. No. 09/680,858 entitled Compositions and Methods for Plant Genetic Modification which is incorporated herein by reference.

Microspore electroporation methods are described in Jardinaud et al., Plant Sci. 93:177-184, 1993, and Fennell and Hauptman, Plant Cell Reports 11:567-570, 1992. Methods for electroporation of MDON into plant protoplasts can also be adapted for use in microspore electroporation.

Whiskers and Microinjection

In yet another alternative embodiment, the recombinagenic oligonucleobase can be delivered to the plant cell by whiskers or microinjection of the plant cell. The so called whiskers technique is performed essentially as described in Frame et al., 1994, Plant J. 6:941-948. The recombinagenic oligonucleobase is added to the whiskers and used to transform the plant cells. The recombinagenic oligonucleobase may be co-incubated with plasmids comprising sequences encoding proteins capable of forming recombinase complexes in plant cells such that recombination is catalyzed between the oligonucleotide and the target sequence.

Selection of Plants

In various embodiments, plants as disclosed herein can be of any species of dicotyledonous, monocotyledonous or gymnospermous plant, including any woody plant species that grows as a tree or shrub, any herbaceous species, or any species that produces edible fruits, seeds or vegetables, or any species that produces colorful or aromatic flowers. For example, the plant maybe selected from a species of plant from the group consisting of canola, sunflower, corn, tobacco, sugar beet, cotton, maize, wheat, barley, rice, alfafa, barley, sorghum, tomato, mango, peach, apple, pear, strawberry, banana, melon, potato, carrot, lettuce, onion, soy bean, soya spp, sugar cane, pea, chickpea, field pea, faba bean, lentils, turnip, rutabaga, brussel sprouts, lupin, cauliflower, kale, field beans, poplar, pine, eucalyptus, grape, citrus, triticale, alfalfa, rye, oats, turf and forage grasses, flax, oilseed rape, mustard, cucumber, morning glory, balsam, pepper, eggplant, marigold, lotus, cabbage, daisy, carnation, tulip, iris, lily, and nut producing plants insofar as they are not already specifically mentioned.

Plants and plant cells can be tested for resistance or tolerance to an herbicide using commonly known methods in the art, e.g., by growing the plant or plant cell in the presence of an herbicide and measuring the rate of growth as compared to the growth rate in the absence of the herbicide.

As used herein, substantially normal growth of a plant, plant organ, plant tissue or plant cell is defined as a growth rate or rate of cell division of the plant, plant organ, plant tissue, or plant cell that is at least 35%, at least 50%, at least 60%, or at least 75% of the growth rate or rate of cell division in a corresponding plant, plant organ, plant tissue or plant cell expressing the wild-type AHAS protein.

As used herein, substantially normal development of a plant, plant organ, plant tissue or plant cell is defined as the occurrence of one or more development events in the plant, plant organ, plant tissue or plant cell that are substantially the same as those occurring in a corresponding plant, plant organ, plant tissue or plant cell expressing the wild-type protein.

In certain embodiments plant organs provided herein include, but are not limited to, leaves, stems, roots, vegetative buds, floral buds, meristems, embryos, cotyledons, endosperm, sepals, petals, pistils, carpels, stamens, anthers, microspores, pollen, pollen tubes, ovules, ovaries and fruits, or sections, slices or discs taken therefrom. Plant tissues include, but are not limited to, callus tissues, ground tissues, vascular tissues, storage tissues, meristematic tissues, leaf tissues, shoot tissues, root tissues, gall tissues, plant tumor tissues, and reproductive tissues. Plant cells include, but are not limited to, isolated cells with cell walls, variously sized aggregates thereof, and protoplasts.

Plants are substantially "tolerant" to a relevant herbicide when they are subjected to it and provide a dose/response curve which is shifted to the right when compared with that provided by similarly subjected non-tolerant like plant. Such dose/response curves have "dose" plotted on the X-axis and "percentage kill", "herbicidal effect", etc., plotted on the y-axis. Tolerant plants will require more herbicide than non-tolerant like plants in order to produce a given herbicidal effect. Plants that are substantially "resistant" to the herbicide exhibit few, if any, necrotic, lytic, chlorotic or other lesions, when subjected to herbicide at concentrations and rates which are typically employed by the agrochemical community to kill weeds in the field. Plants which are resistant to an herbicide are also tolerant of the herbicide.

Generation of Plants

Tissue culture of various tissues of plant species and regeneration of plants therefrom is known. For example, the propagation of a canola cultivar by tissue culture is described in any of the following but not limited to any of the following: Chuong et al., "A Simple Culture Method for *Brassica* hypocotyls Protoplasts," Plant Cell Reports 4:4-6, 1985; Barsby, T. L., et al., "A Rapid and Efficient Alternative Procedure for the Regeneration of Plants from Hypocotyl Protoplasts of *Brassica napus*," Plant Cell Reports (Spring, 1996); Kartha, K., et al., "In vitro Plant Formation from Stem Explants of Rape," Physiol. Plant, 31:217-220, 1974; Narasimhulu, S., et al., "Species Specific Shoot Regeneration Response of Cotyledonary Explants of Brassicas," Plant Cell Reports (Spring 1988); Swanson, E., "Microspore Culture in *Brassica*," Methods in Molecular Biology, Vol. 6, Chapter 17, p. 159, 1990.

Further reproduction of the variety can occur by tissue culture and regeneration. Tissue culture of various tissues of soybeans and regeneration of plants therefrom is well known and widely published. For example, reference may be had to Komatsuda, T. et al., "Genotype X Sucrose Interactions for Somatic Embryogenesis in Soybeans," Crop Sci. 31:333-337, 1991; Stephens, P. A., et al., "Agronomic Evaluation of Tissue-Culture-Derived Soybean Plants," Theor. Appl. Genet. 82:633-635, 1991; Komatsuda, T. et al., "Maturation and Germination of Somatic Embryos as Affected by Sucrose and Plant Growth Regulators in Soybeans *Glycine gracilis* Skvortz and *Glycine max* (L.) Merr." Plant Cell, Tissue and Organ Culture, 28:103-113, 1992; Dhir, S. et al., "Regeneration of Fertile Plants from Protoplasts of Soybean (*Glycine max* L. Merr.); Genotypic Differences in Culture Response," Plant Cell Reports 11:285-289, 1992; Pandey, P. et al., "Plant Regeneration from Leaf and Hypocotyl Explants of *Glycine wightii* (W. and A.) VERDC. var. longicauda," Japan J. Breed. 42:1-5, 1992; and Shetty, K., et al., "Stimulation of In Vitro Shoot Organogenesis in *Glycine max* (Merrill.) by Allantoin and Amides," Plant Science 81:245-251, 1992. The disclosures of U.S. Pat. No. 5,024,944 issued Jun. 18, 1991 to Collins et al., and U.S. Pat. No. 5,008,200 issued Apr. 16, 1991 to Ranch et al., are hereby incorporated herein in their entirety by reference.

The following example and FIGS. 4-13 illustrate the practice of the present invention but should not be construed as limiting its scope.

Example 1: Dramatically improved conversion of a blue fluorescent protein (BFP) gene in transgenic *Arabidopsis thaliana* cells to a green fluorescing protein (GFP) by introducing a targeted single nucleotide mutation through Gene Repair Oligoucleotides (GRONs) in combination with a Transcription Activator-Like Effector Nuclease (TALEN) pair that cleaves near the targeted base change.

An *Arabidopsis* line with multiple copies of a blue fluorescent protein gene was created by methods known to those skilled in the art (see, e.g., Clough and Brent, 1998). Root-derived meristematic tissue cultures were established with this line, which was used for protoplast isolation and culture (see, e.g., Mathur et al., 1995). GRON delivery into protoplasts was achieved through polyethylene glycol (PEG) mediated GRON uptake into protoplasts. A method using a 96-well format, similar to that described by similar to that described by Fujiwara and Kato (2007) was used. In the following the protocol is briefly described. The volumes given are those applied to individual wells of a 96-well dish.

1. Mix 6.25 µl of GRON/TALEN mix (80 µM BFP4 Coding/41mer GRON) with 25 µl of *Arabidopsis* BFP transgenic root meristematic tissue-derived protoplasts at $5\times10^6$ cells/ml in each well of a 96 well plate.
2. 31.25 µl of a 40% PEG solution was added and the protoplasts were mixed.
3. Treated cells were incubated on ice for 30 min.
4. To each well 200 µl of W5 solution was added and the cells mixed.
5. The plates were allowed to incubate on ice for 30 min allowing the protoplasts to settle to the bottom of each well.
6. 200 µl of the medium above the settled protoplasts was removed.
7. 85 µl of culture medium (MSAP, see Mathur et al., 1995) was added.
8. The plates were incubated at room temperate in the dark for 48 hours. The final concentration of GRON after adding culture medium is 8 µM.

Using this protocol, TALEN plasmids at different concentrations were introduced together with GRON. Forty eight hours after GRON delivery samples were analyzed by flow cytometry in order to detect protoplasts whose green and yellow fluorescence is different from that of control protoplasts. The green fluorescence is caused by the introduction of a targeted mutation in the BFP gene, resulting in the synthesis of GFP. The results are shown in FIG. 1.

FIG. 1. Root meristematic tissue-derived protoplasts were treated with TALEN plasmids at various concentrations together with GRON targeting a mutation in the BFP gene, causing a conversion into a GFP gene. GFP expression was measured by flow cytometry 48 h after GRON/TALEN delivery For FIGS. 4-13, the following Legend applies:
GRONs
BFP→GFP Targeting Designs.

```
BFP->GFP H66Y CAC->TAC.
BFP4/C/41/5'Cy3/3'idC (SEQ ID NO: 1):
VCCCTCGTGACCACCTTCACCTACGGCGTGCAGTGCTTCAGCH

BFP4/NC/41/5'Cy3/3'idC (SEQ ID NO: 2):
VGCTGAAGCACTGCACGCCGTAGGTGAAGGTGGTCACGAGGGH
```

BFP Non-Targeting Control Designs.

Figure 3:
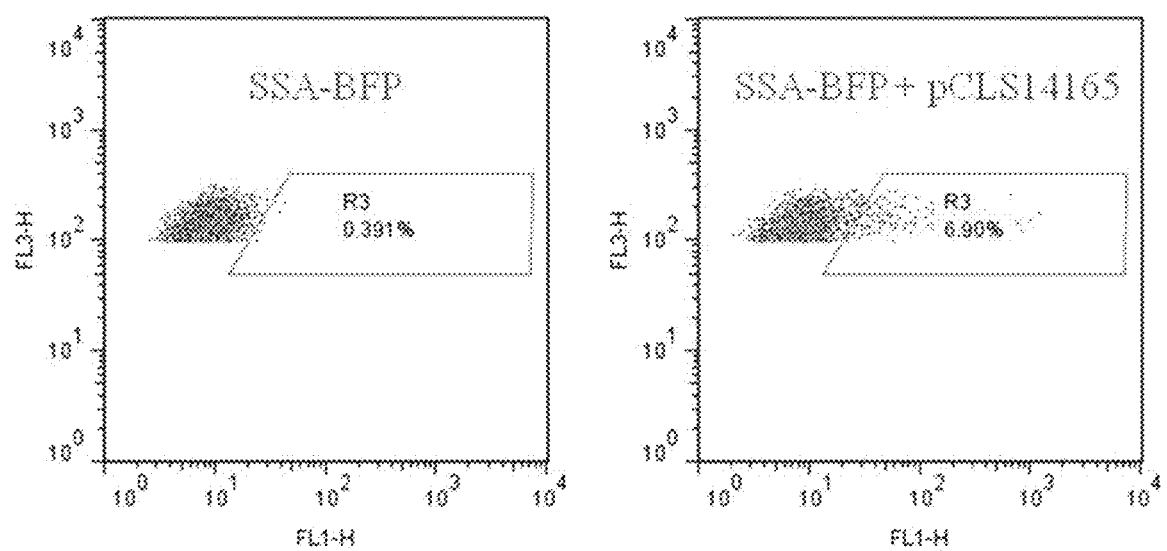
FIG. 3 depicts the introduction of double strand breaks in a target sequence mediate by TALEN plasmid pCLS14165 as measured by flow cytometry in a single strand annealing assay.
Figure 4:
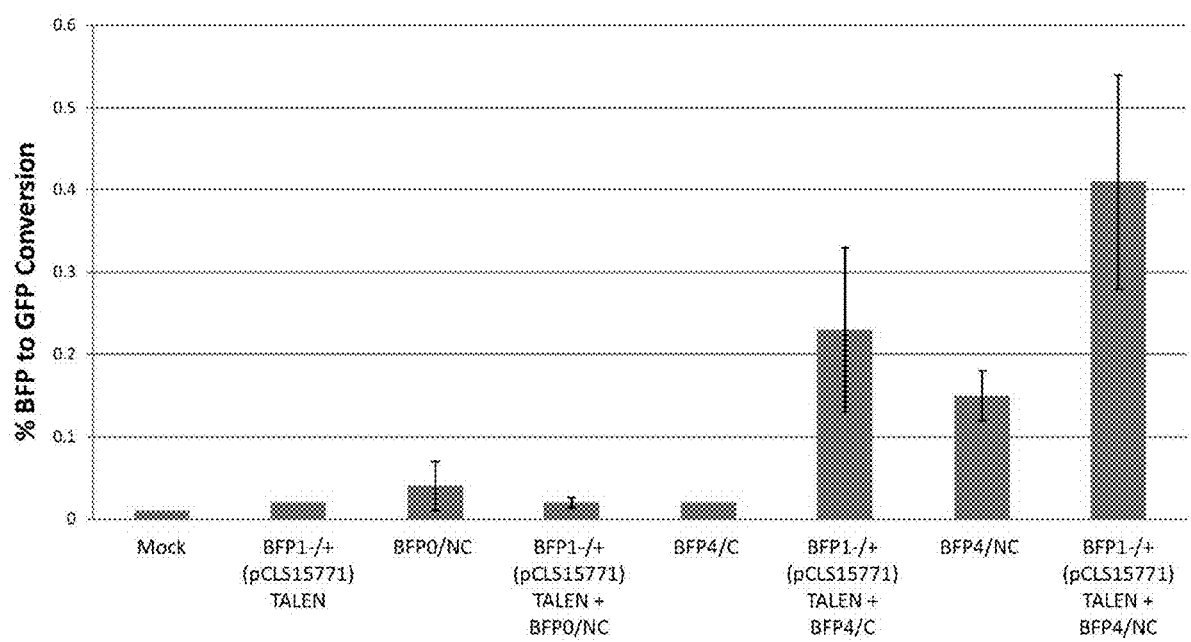
FIG. 4 depicts the percent GFP to BFP conversion mediated by TALEN nickase (plasmid pCLS15771) alone, coding and non-coding GRON, and a combination of GRON plus TALEN.
Figure 5:
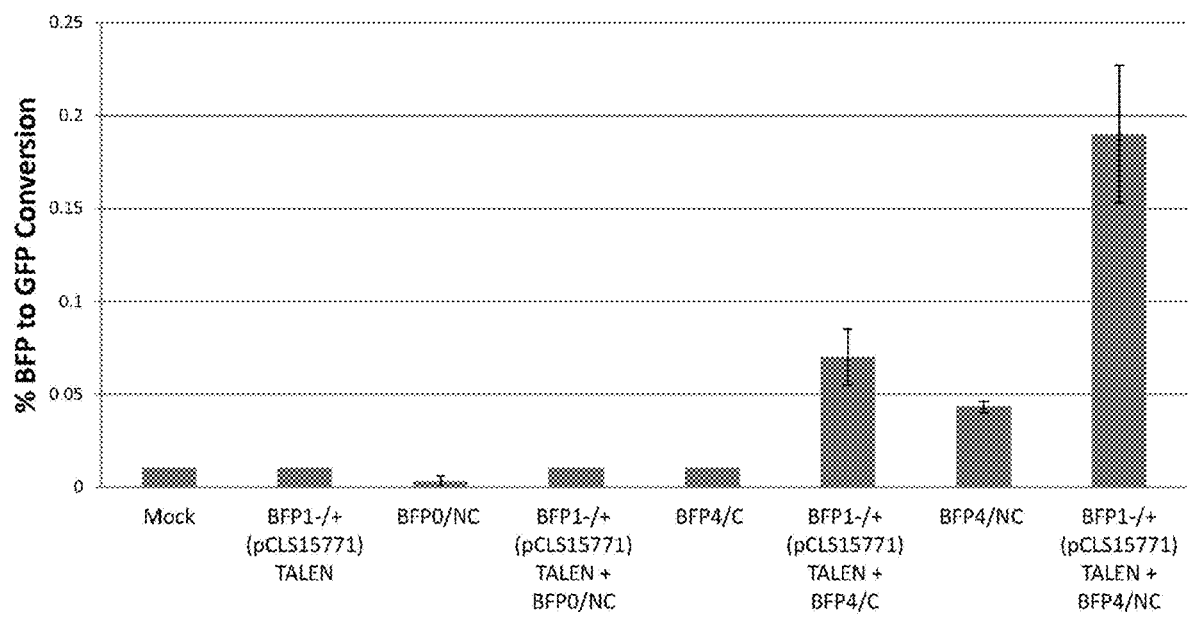
FIG. 5 depicts the percent GFP to BFP conversion mediated by TALEN nickase (plasmid pCLS15771) alone, coding and non-coding GRON, and a combination of GRON plus TALEN.
Figure 6:
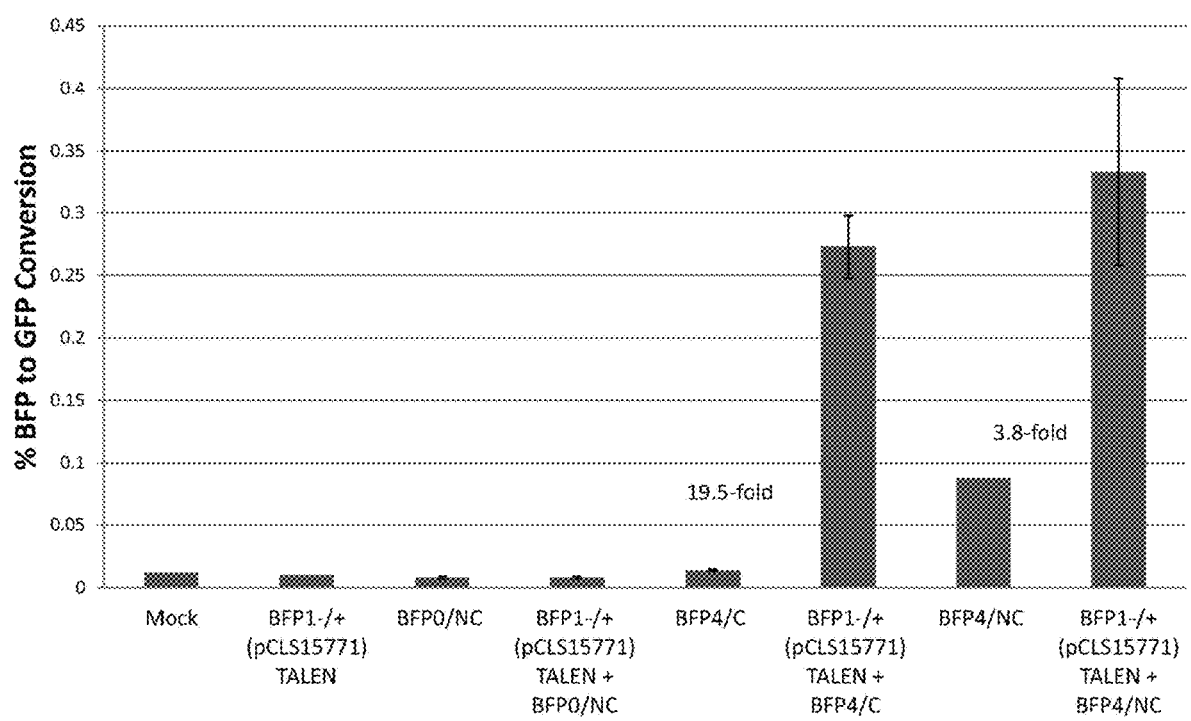
FIG. 6 depicts the percent GFP to BFP conversion mediated by TALEN nickase (plasmid pCLS15771) alone, coding and non-coding GRON, and a combination of GRON plus TALEN.
Figure 7:
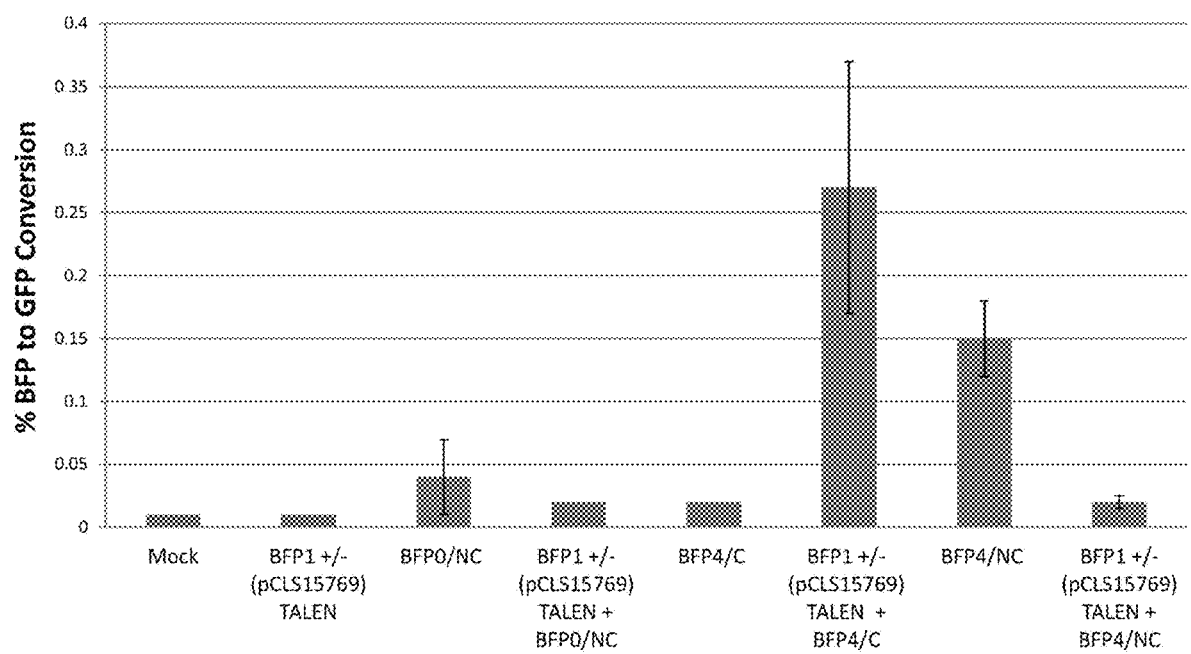
FIG. 7 depicts the percent GFP to BFP conversion mediated by TALEN nickase (plasmid pCLS15769) alone, coding and non-coding GRON, and a combination of GRON plus TALEN.
Figure 8:
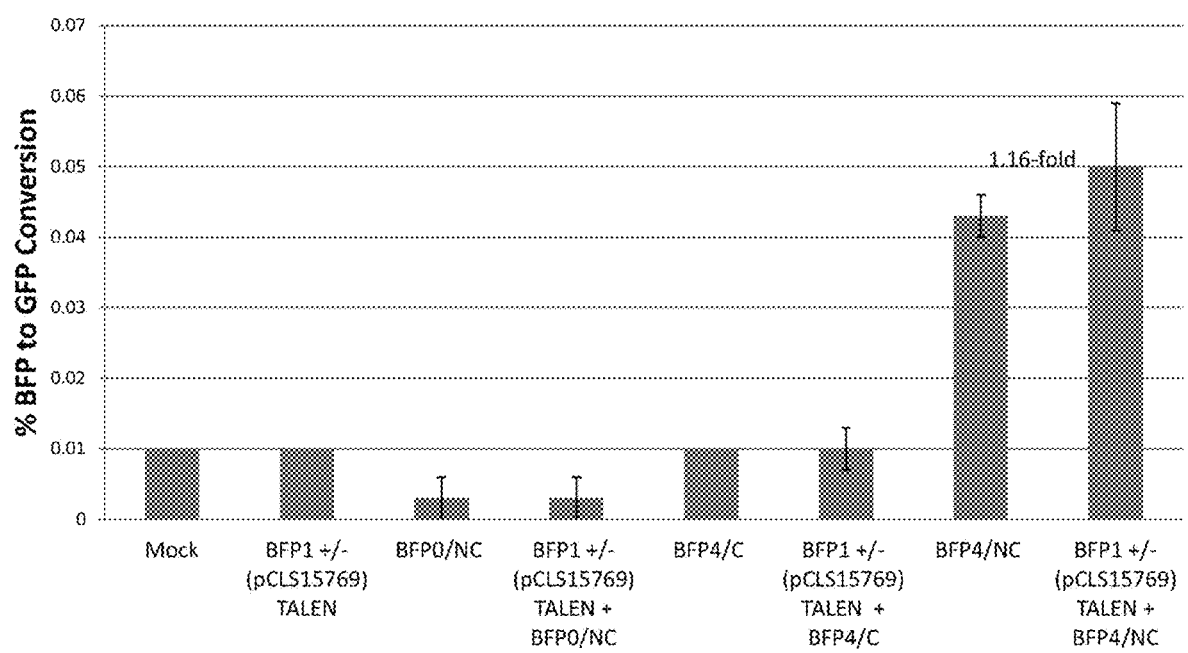
FIG. 8 depicts the percent GFP to BFP conversion mediated by TALEN nickase (plasmid pCLS15769) alone, coding and non-coding GRON, and a combination of GRON plus TALEN.
Figure 9:
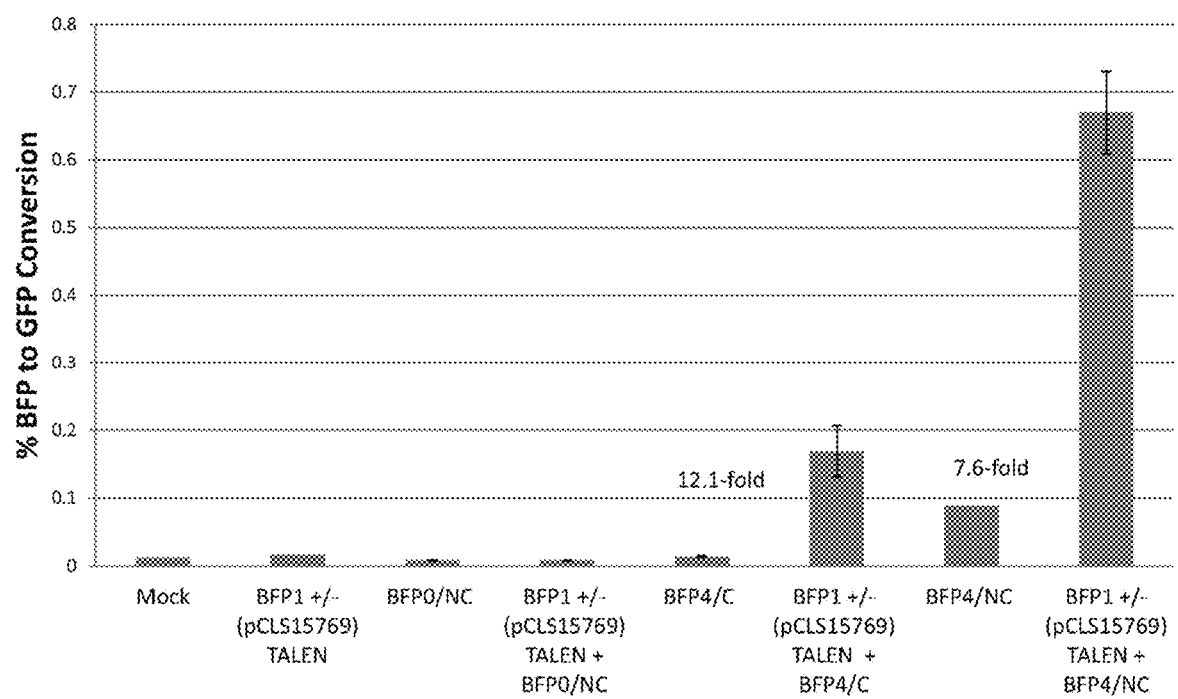
FIG. 9 depicts the percent GFP to BFP conversion mediated by TALEN nickase (plasmid pCLS15769) alone, coding and non-coding GRON, and a combination of GRON plus TALEN.
Figure 10:
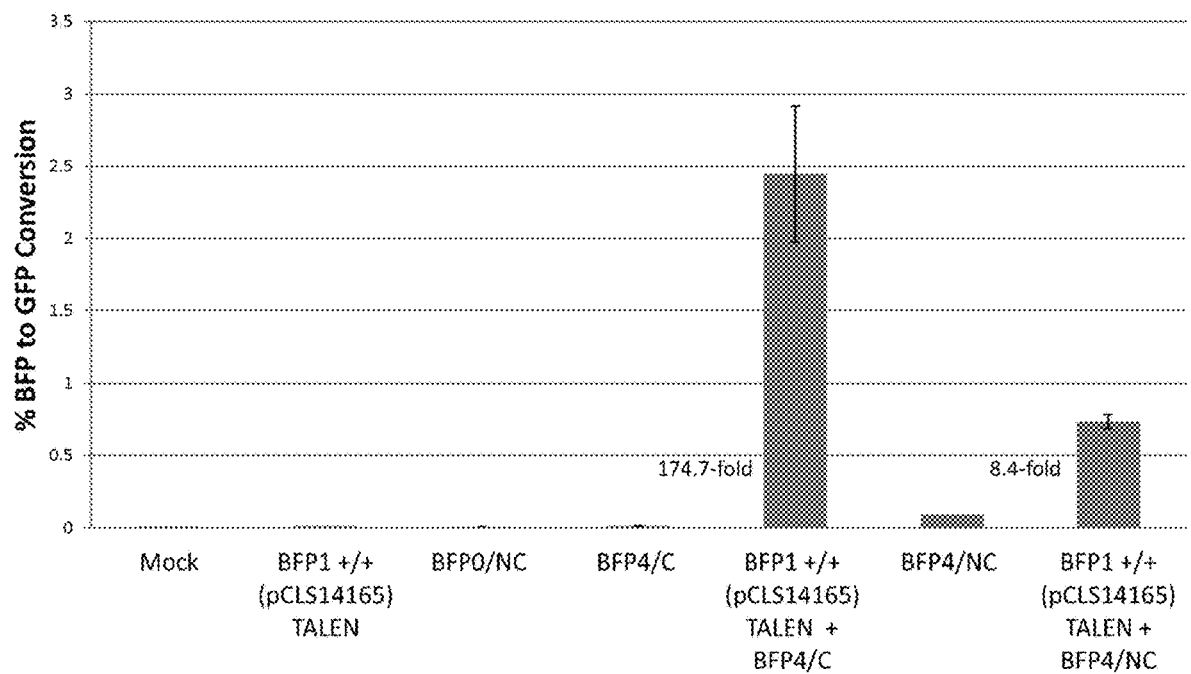
FIG. 10 depicts the percent GFP to BFP conversion mediated by TALEN double strand breaker (plasmid pCLS14165) alone, coding and non-coding GRON, and a combination of GRON plus TALEN.
Figure 11:
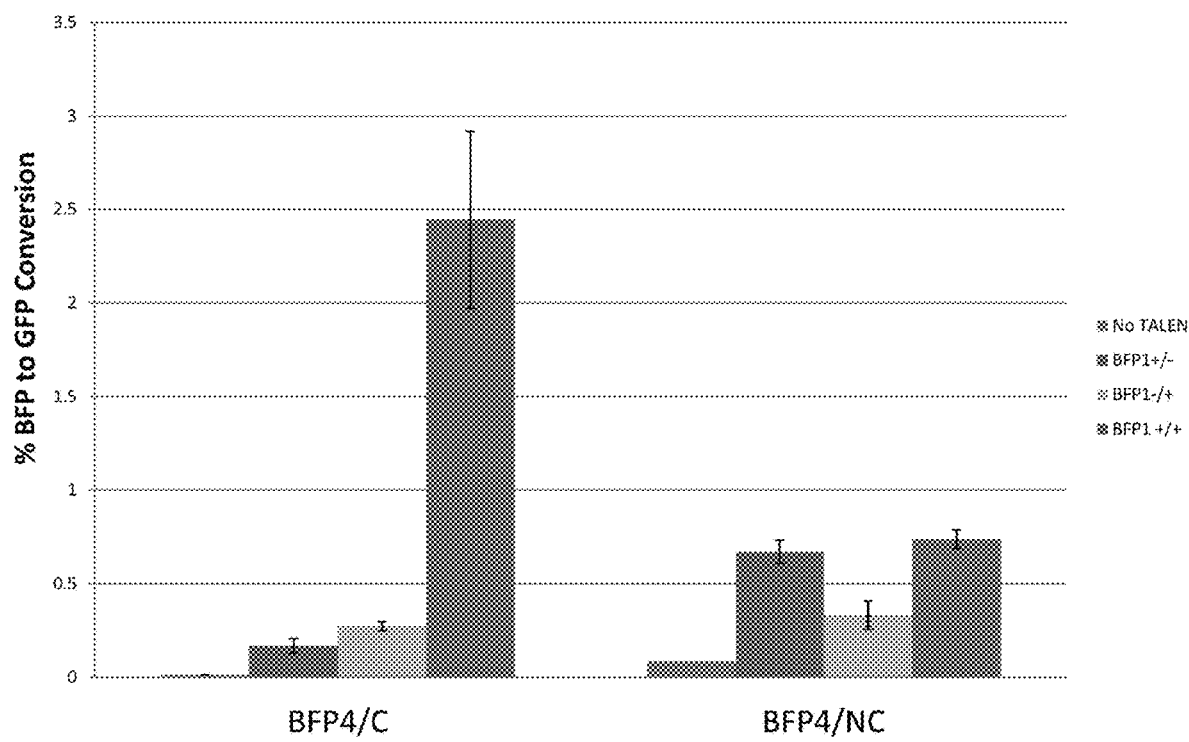
FIG. 11 depicts the percent GFP to BFP conversion mediated by TALEN alone, coding and non-coding GRON, and a combination of GRON plus TALEN.
Figure 12:
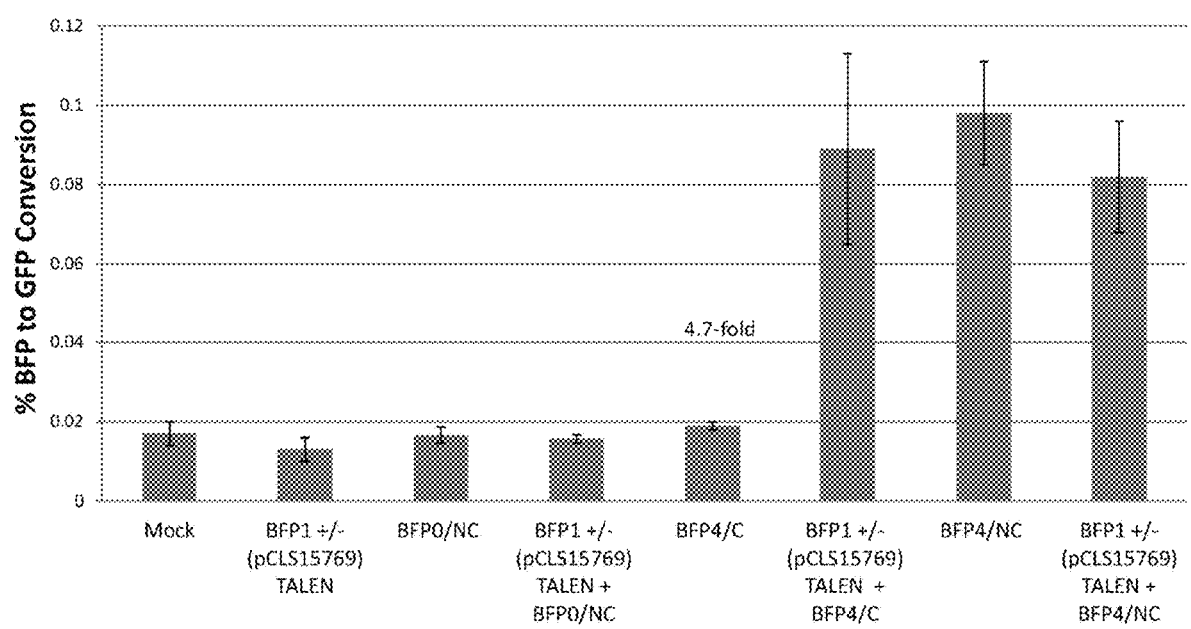
FIG. 12 depicts the percent GFP to BFP conversion mediated by TALEN nickase (plasmid pCLS15769) alone, coding and non-coding GRON, and a combination of GRON plus TALEN.
Figure 13:
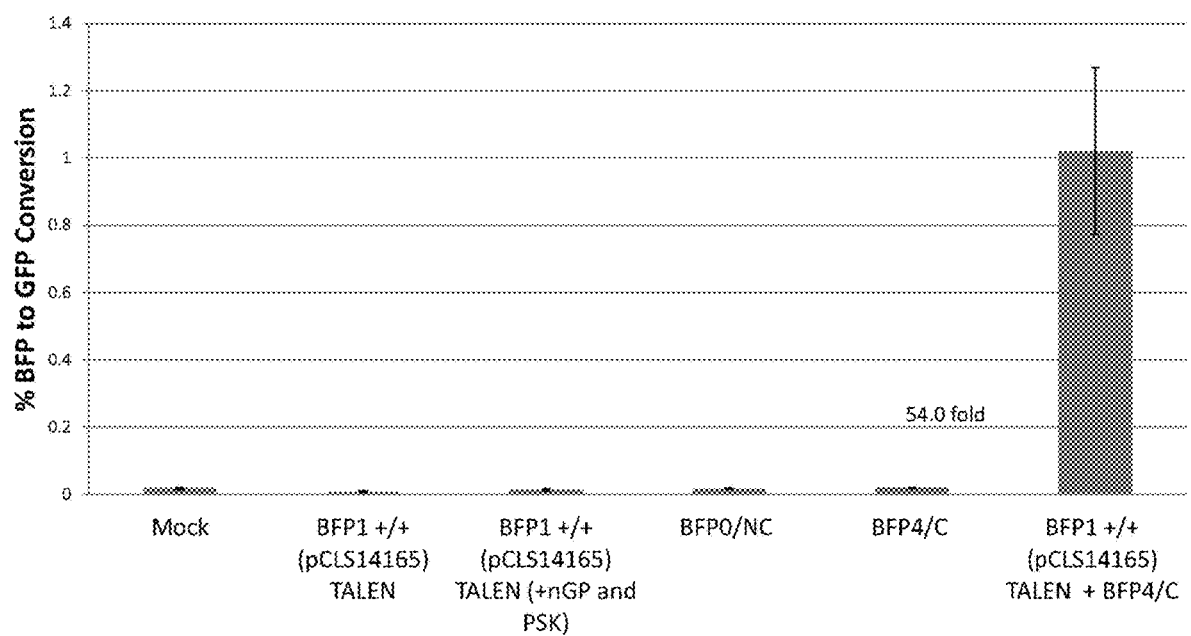
FIG. 13 depicts the percent GFP to BFP conversion mediated by TALEN nickase (plasmid pCLS15769) alone, coding and non-coding GRON, and a combination of GRON plus TALEN.

```
BFP H66-CAC
BFP0/C/41/5'3PS/3'3PS (SEQ ID NO: 3):
VCCCTCGTGACCACCTTCACCCACGGCGTGCAGTGCTTCAGCH
BFP0/NC/41/5'3PS/3'3PS (SEQ ID NO: 4):
VGCTGAAGCACTGCACGCCGTGGGTGAAGGTGGTCACGAGGGH
``` pCLS14165 has both TAL arms (designed as per Zhang et al., 2013) on a single plasmid with each arm binding to the underlined sequence and linked to a FokI monomer. This combination produces a double strand break (DSB) as shown in FIG. 3 in the single strand annealling assay (SSA) performed in the same was as the ones in Zhang et al. (2013)

pCLS15771 is a nickase with a mutation (D450A) in the FokI domain for the left arm. The right arm in this construct is as per pCLS14165.

pCLS15769 is a nickase with a mutation (D450A) in the FokI domain for the right arm. The left arm in this construct is as per pCLS14165.

The GRONs and TALENs were tested as shown in FIGS. 4-13. The control treatments consisting of non-targeting GRONs (BFP0/C or BFP0/NC) and TALENs alone as well as mock treatments with the 40% PEG solution lacking GRONs or TALEN plasmid had no significant conversion activity.

In this system the BFP4/NC GRON design alone is better than the BFP4/C GRON design alone. Combining these with the DSB TALEN (pCLS14165) improves both with the best activity and fold improvement (in many cases >2 orders of magnitude) with the BFP4/C GRON. Significant improvement are also observed in combining GRONs with nickase TALEN pairs and are expected to be most beneficial by minimizing collateral damage when mutations are targeted in several genes/loci/alleles simultaneously.

REFERENCES

Clough, S. J., and Bent, A. F. (1998). Floral dip: A simplified method for *Agrobacterium*-mediated transformation of *Arabidopsis thaliana*. Plant J. 16, 735-743.

Mathur, J., Szabados, L, and Koncz, C. (1995) A simple method for isolation, liquid culture, transformation and regeneration of *Arabidopsis thaliana* protoplasts. Plant Cell Rep. 14, 221-226

Fujikawa Y, Kato N (2007) Split luciferase complementation assay to study protein-protein interactions in *Arabidopsis* protoplasts. Plant J 52: 185-195

Zhang Y, Zhang F, Li X, Baller J A, Qi Y, Starker C G, Bogdanove A J, Voytas D F. (2013) Transcription activator-like effector nucleases enable efficient plant genome engineering. Plant Physiol. 161(1):20-7.

We claim:

1. A method for introducing a gene repair oligonucleobase (GRON)-mediated mutation into a target deoxyribonucleic acid (DNA) sequence in a plant cell, comprising:
   delivering a GRON into the plant cell, wherein the GRON comprises a sequence that encodes the mutation to be introduced into the target DNA sequence; and
   culturing the plant cell under conditions that increase one or more cellular DNA repair processes prior to, and/or coincident with, delivery of a GRON into the plant cell to introduce the mutation into the target DNA sequence,
   wherein the conditions that increase one or more cellular DNA repair processes comprise introducing one or more site-specific TALEN endonucleases which induce single strand nicks or double DNA strand breaks into the plant cell, and
   wherein the GRON is single stranded and comprises a 3' blocking substituent and a 5' blocking constituent, each blocking substituent comprising phosphorothioate or phosphoamidate internucleotide linkages, wherein the internucleotide linkages of the GRON that are not part of the 3' blocking substituent and the 5' blocking constituent are unmodified phosphodiester bonds.

2. The method of claim 1, wherein the one or more site-specific endonucleases which induce single strand nicks or double DNA strand breaks are covalently coupled to the GRON.

3. The method of claim 1, wherein the plant cell is a cell from a plant selected from the group consisting of canola, sunflower, corn, tobacco, sugar beet, cotton, maize, wheat, barley, rice, alfafa, barley, sorghum, tomato, mango, peach, apple, pear, strawberry, banana, melon, potato, carrot, lettuce, onion, soy bean, sugar cane, pea, chickpea, field pea, fava bean, lentil, turnip, rutabaga, brussel sprout, lupin, cauliflower, kale, field bean, poplar, pine, eucalyptus, grape, citrus, triticale, alfalfa, rye, oats, turf grass, forage grass, flax, oilseed rape, mustard, cucumber, morning glory, balsam, pepper, eggplant, marigold, lotus, cabbage, daisy, carnation, tulip, iris, and lily.

4. The method of claim 1, wherein the plant cell is transgenic.

5. The method of claim 4, wherein the target DNA sequence is an endogenous gene of the plant cell.

6. The method of claim 1, further comprising regenerating a plant having the mutation introduced by the GRON from the plant cell.

7. The method of claim 6, further comprising collecting seeds from the plant.

\* \* \* \* \*